US010185811B2

(12) United States Patent
Dixit et al.

(10) Patent No.: US 10,185,811 B2
(45) Date of Patent: Jan. 22, 2019

(54) PILL REMOVAL DETECTION FROM PILL PACKAGE

(71) Applicant: EMPIRE TECHNOLOGY DEVELOPMENT LLC, Wilmington, DE (US)

(72) Inventors: Mandar Shirish Dixit, Pune (IN); Mona Sharma, Jabalpur (IN); Himanshu Mishra, Bangalore (IN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 530 days.

(21) Appl. No.: 14/933,049

(22) Filed: Nov. 5, 2015

(65) Prior Publication Data
US 2016/0132661 A1   May 12, 2016

(30) Foreign Application Priority Data

Nov. 6, 2014  (IN) ............................ 5598/CHE/2014

(51) Int. Cl.
*G08B 13/14* (2006.01)
*G06F 19/00* (2018.01)
(Continued)

(52) U.S. Cl.
CPC ............ *G06F 19/3462* (2013.01); *A61J 1/16* (2013.01); *G06F 19/00* (2013.01); *A61J 1/035* (2013.01); *A61J 7/0418* (2015.05); *A61J 2200/30* (2013.01)

(58) Field of Classification Search
CPC ........ G06F 19/3462; G06F 19/00; A61J 1/16; A61J 2200/30; A61J 1/035; A61J 7/0418;
(Continued)

(56) References Cited

U.S. PATENT DOCUMENTS 5,412,372 A *  5/1995  Parkhurst .............. A61J 7/0481
                                                    221/15
7,113,101 B2   9/2006  Petersen et al.
(Continued)

FOREIGN PATENT DOCUMENTS

WO         9714157 A1    4/1997
WO      2010108838 A1    9/2010

*Primary Examiner* — Anh V La
(74) *Attorney, Agent, or Firm* — IP Spring

(57) ABSTRACT

Technologies are generally provided for a pill dispensing device to track removal of a pill from a pill package. The device may include circuits printed/embedded on a composite sheet configured to be locally or completely flexible/stretchable with a multitude of slits corresponding to locations of pill containing cavities of the pill package. Composite sheet may include embedded rigid sections and be flexible near the slits. Additionally, top and/or bottom plates may further provide structural rigidity to achieve desired flexible behavior of the composite sheet. Electronic circuits printed/embedded on or in the composite sheet may detect removal of a pill from the pill package through the slits. Slits may include electrical contacts configured to switch a circuit corresponding to each slit between an active and an inactive state. Upon removal of the pill, the contacts may separate or touch each other, opening or closing the circuit corresponding to the expanded slit.

20 Claims, 17 Drawing Sheets

(51) Int. Cl.
*A61J 1/16* (2006.01)
*A61J 1/03* (2006.01)
*A61J 7/04* (2006.01)

(58) Field of Classification Search
CPC .... A61J 7/0481; A61J 7/0409; A61J 2205/20; A61J 7/0436; H05K 1/118; H05K 3/1275; H05K 1/0269; H05K 2203/1545; H05K 1/16; H05K 1/0287; Y10T 29/49155
USPC .......... 340/568.1, 590, 572.7; 221/2; 368/10
See application file for complete search history.

(56) References Cited

U.S. PATENT DOCUMENTS

| | | |
|---|---|---|
| 8,120,492 B2 | 2/2012 | Scharfeld et al. |
| 8,389,862 B2 | 3/2013 | Arora et al. |
| 2005/0241983 A1* | 11/2005 | Snyder .................. A61J 7/0481 206/539 |
| 2006/0144747 A1* | 7/2006 | Le .......................... A61J 7/0481 206/531 |
| 2009/0184023 A1* | 7/2009 | Brollier .................... A61J 1/035 206/531 |
| 2013/0285681 A1* | 10/2013 | Wilson ..................... G01N 27/00 324/693 |
| 2013/0319902 A1* | 12/2013 | Tufi ......................... A61J 1/035 206/534 |

* cited by examiner

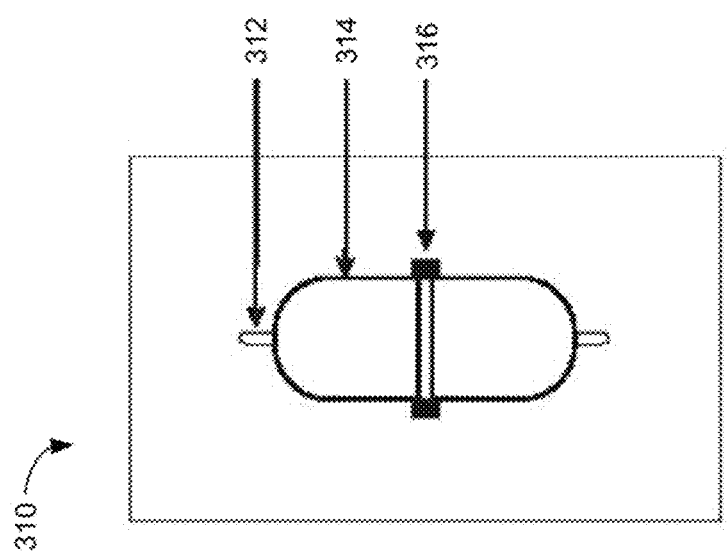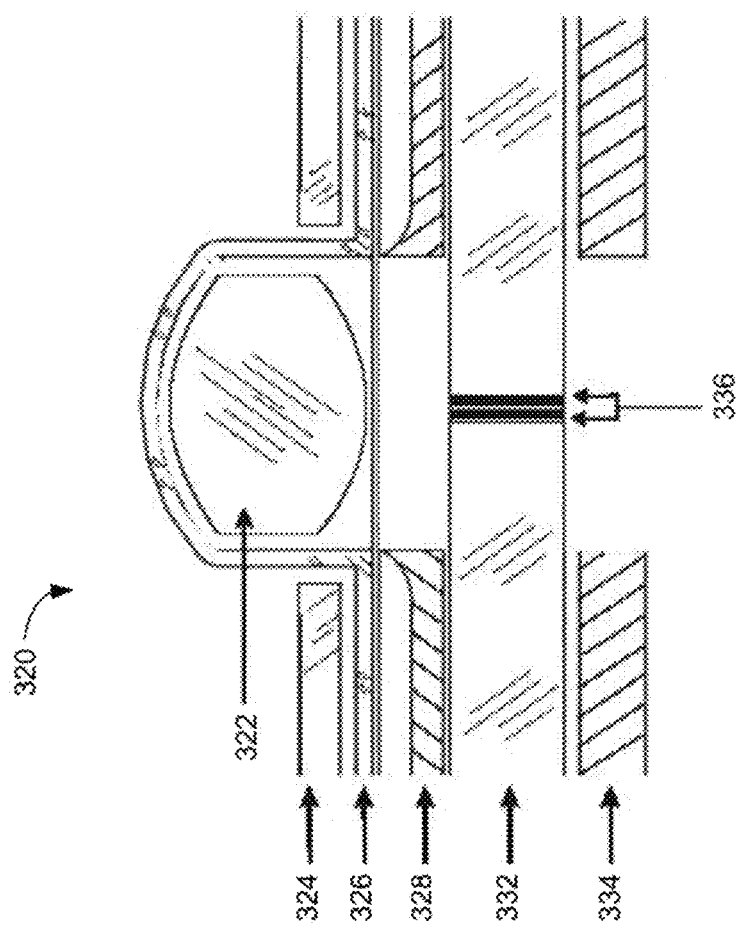
FIG. 3

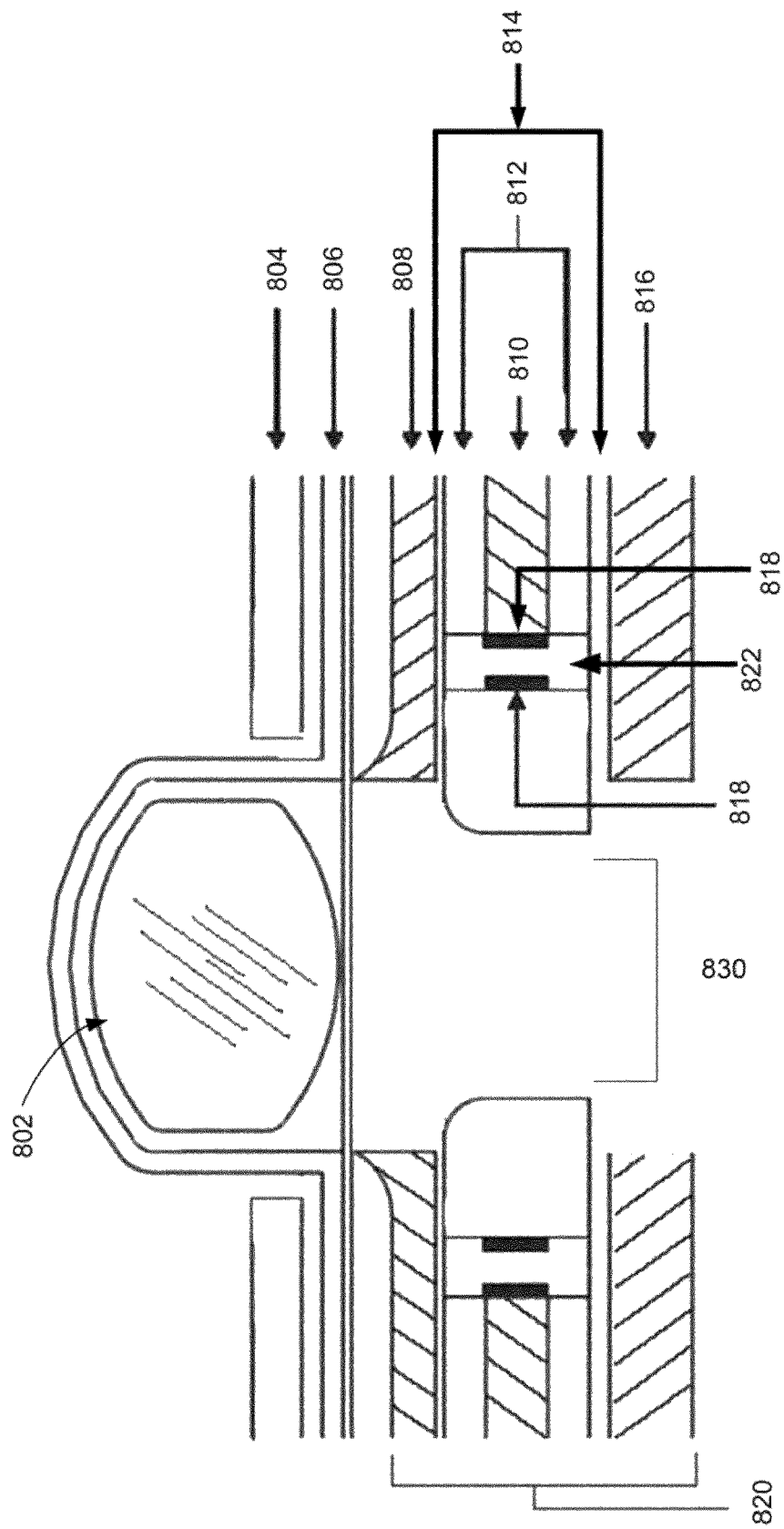

COMPUTER PROGRAM PRODUCT 1400

SIGNAL-BEARING MEDIUM 1402

1404 AT LEAST ONE OF

ONE OR MORE INSTRUCTIONS TO FORM A RIGID UPPER PORTION CONFIGURED TO ACCOMMODATE INSERTION OF A PILL PACKAGE;
    ONE OR MORE INSTRUCTIONS TO PRINT A CIRCUIT BOARD ON A COMPOSITE SHEET, THE CIRCUIT BOARD INCLUDING A PLURALITY OF INDIVIDUAL CIRCUITS;
    ONE OR MORE INSTRUCTIONS TO FORM A PLURALITY OF SLITS IN EACH INDIVIDUAL CIRCUIT OF THE CIRCUIT BOARD ON THE COMPOSITE SHEET;
    ONE OR MORE INSTRUCTIONS TO INSERT THE COMPOSITE SHEET INCLUDING THE PRINTED CIRCUIT BOARD BETWEEN A TOP PLATE AND A BOTTOM PLATE, EACH OF THE TOP PLATE AND THE BOTTOM PLATE INCLUDING A PLURALITY OF OPENINGS CORRESPONDING TO A LOCATION OF THE PLURALITY OF SLITS FORMED ON THE COMPOSITE SHEET;
    ONE OR MORE INSTRUCTIONS TO INSERT THE PRINTED CIRCUIT BOARD SANDWICHED BETWEEN THE TOP PLATE AND THE BOTTOM PLATE WITHIN THE UPPER PORTION; AND/OR
    ONE OR MORE INSTRUCTIONS TO INSERT THE PILL PACKAGE BETWEEN THE UPPER PORTION AND THE COMPOSITE SHEET, SUCH THAT EACH OF A PLURALITY OF PILL CONTAINING CAVITIES IN THE PILL PACKAGE CORRESPOND TO THE PLURALITY OF SLITS FORMED IN THE COMPOSITE SHEET.

| COMPUTER-READABLE MEDIUM 1406 | RECORDABLE MEDIUM 1408 | COMMUNICATIONS MEDIUM 1410 |
|---|---|---|

FIG. 14

PILL REMOVAL DETECTION FROM PILL PACKAGE

CROSS-REFERENCE TO RELATED APPLICATION

This application claims priority under 35 U.S.C. § 119(a) of India Application No. 5598/CHE/2014 filed on Nov. 6, 2014. The India Application is hereby incorporated by reference in its entirety.

BACKGROUND

Unless otherwise indicated herein, the materials described in this section are not prior art to the claims in this application and are not admitted to be prior art by inclusion in this section.

Electronic pill boxes may enable monitoring patient compliance in taking medications. Some electronic pill boxes may alert patients to take a pill at a particular dosage time, may keep track of missed dosages, and may alert third parties of patient compliance. Some features of electronic pill boxes include pill removal detection from a pill package such as a blister pack incorporated with the electronic pill box, processing detected pill removal as pill removal events, and storing and communication of the pill removal events. Reliability and durability of electronic pill boxes may be a challenge, and current designs may be costly and inefficient. For example, printable electronics employing printable conductive ink may enable direct printing of frangible circuits on a blister pack such that a pill removal event is recorded via the breaking of individual frangible circuits on the blister pack. Frangible circuits may only be used once, and a new printed circuit board may need to be provided for reuse, increasing recurring costs and reducing the reliability of the pill box over repeated cycles of use. Additionally, the flexibility of printable paper circuit boards makes connections to rigid components less reliable, and conductive ink lines may crack due to multiple bending events.

SUMMARY

The following summary is illustrative only and is not intended to be in any way limiting. In addition to the illustrative aspects, examples, and features described above, further aspects, examples, and features will become apparent by reference to the drawings and the following detailed description.

The present disclosure generally describes an example pill dispensing device. The example pill dispensing device may monitor pill removal. The example pill dispensing device may include, among other things, an upper portion including a plurality of cavities, a lower portion formed from a locally or completely flexible or stretchable composite sheet, and a circuit board printed on or embedded into the composite sheet. The upper portion may be configured to accommodate insertion of a pill package. The composite sheet may include a plurality of slits corresponding to a location of the plurality of cavities of the upper portion. The lower portion may further include a top plate and a bottom plate, where each of the top plate and the bottom plate may include a plurality of openings corresponding to a location of the plurality of slits formed on the composite sheet. The circuit board may include one or more circuits, which may be used to detect removal of pills through the plurality of slits in the composite sheet.

The present disclosure also generally describes an example system. The example system may monitor pill removal from a pill dispensing device. The system may include a pill dispensing device, a controller configured to detect a change in a state of the one or more circuits in response to removal of a pill from a cavity of the pill package through the slit in the lower portion, and a remote monitoring service configured to store a record of removal of the pill from the pill dispensing device. The pill dispensing device may include, at least, an upper portion including a plurality of cavities, a lower portion formed from a locally or completely flexible or stretchable composite sheet, and a circuit board printed on or embedded into the composite sheet. The upper portion may be configured to accommodate insertion of a pill package. The composite sheet may include a plurality of slits corresponding to a location of the plurality of cavities of the upper portion. The lower portion may be sandwiched between a top plate and a bottom plate, where each of the top plate and the bottom plate may include a plurality of openings corresponding to a location of the plurality of slits formed on the composite sheet. The circuit board may include one or more circuits to detect removal of pills through the plurality of slits in the composite sheet.

The present disclosure further describes an example method. The example method may manufacture a pill dispensing device to monitor pill removal. The example method may include, among other things, forming a rigid upper portion configured to accommodate insertion of a pill package and one of printing a circuit board on a composite sheet or embedding the circuit board into the composite sheet, where the circuit board may include a plurality of individual circuits. The example method may additionally include forming a plurality of slits in each individual circuit of the circuit board on the composite sheet and inserting the composite sheet including the printed circuit board between a top plate and a bottom plate, where each of the top plate and the bottom plate may include a plurality of openings corresponding to a location of the plurality of slits formed on the composite sheet. The example method may further include inserting the printed circuit board sandwiched between the top plate and the bottom plate within the upper portion and inserting the pill package between the upper portion and the composite sheet, such that each of a plurality of pill containing cavities in the pill package correspond to the plurality of slits formed in the composite sheet.

BRIEF DESCRIPTION OF THE DRAWINGS

The foregoing and other features of this disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which:

FIG. 3 illustrates a sectional view of an assembled pill dispensing device;

FIG. 8 illustrates a section view of an assembled pill dispensing device;

FIG. 14 illustrates a block diagram of an example computer program product, all arranged in accordance with at least some examples as described herein.

DETAILED DESCRIPTION

Figure 1:
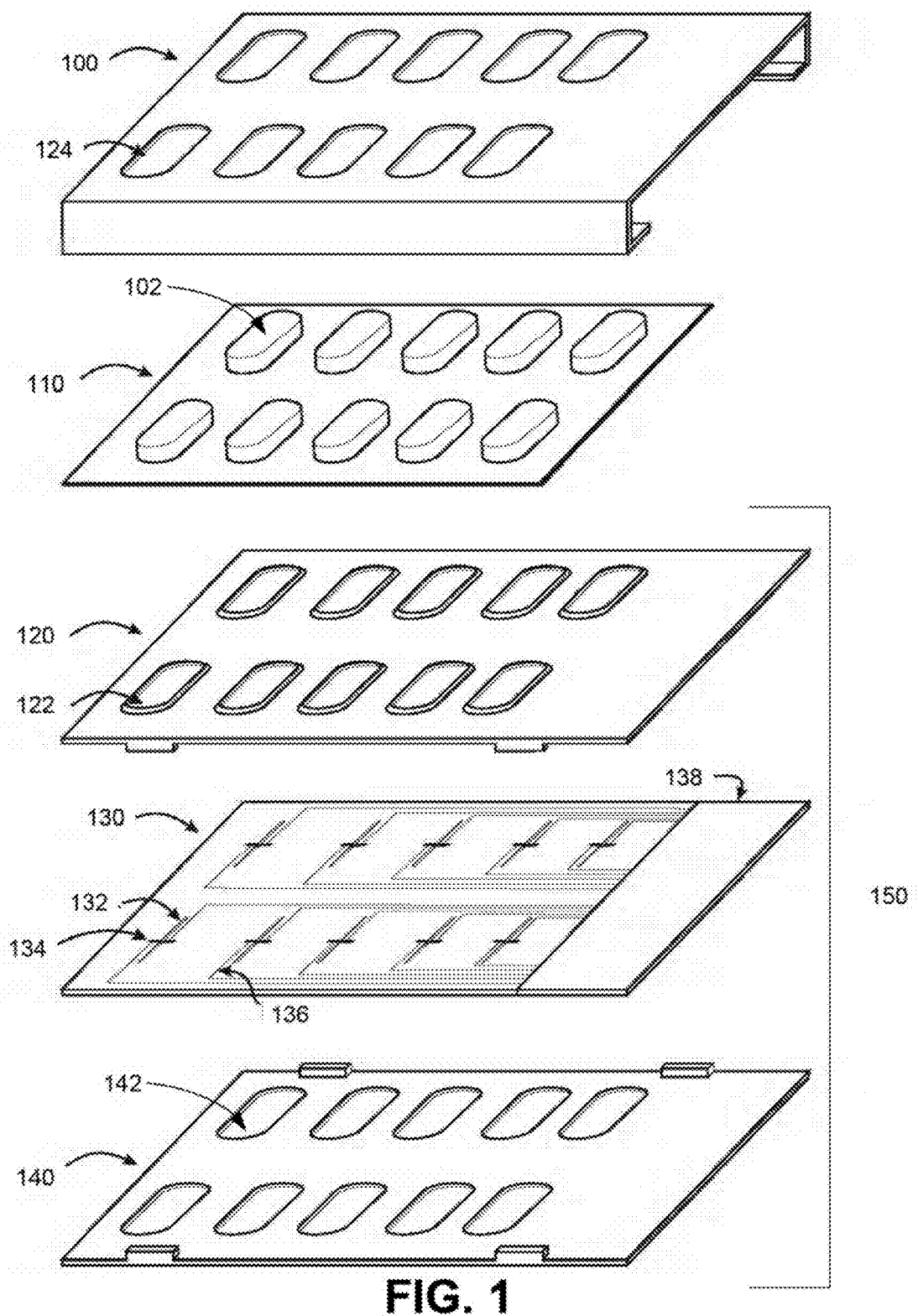
FIG. 1 illustrates an example pill dispensing device including an upper portion, a circuit board printed on a lower portion, and a pill package.

In the following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to compositions, methods, apparatus, systems, devices, and/or computer program products related to detecting pill removal from a pill package.

Briefly stated, technologies are generally provided for a pill dispensing device to track removal of a pill from a pill package. The device may include circuits printed/embedded on a composite sheet configured to be locally or completely flexible/stretchable with a multitude of slits corresponding to locations of pill containing cavities of the pill package. Composite sheet may include embedded rigid sections and be flexible near the slits. Additionally, top and/or bottom plates may further provide structural rigidity to achieve desired flexible behavior of the composite sheet. Electronic circuits printed/embedded on or in the composite sheet may detect removal of a pill from the pill package through the slits. Slits may include electrical contacts configured to switch a circuit corresponding to each slit between an active and an inactive state. Upon removal of the pill, the contacts may separate or touch each other, opening or closing the circuit corresponding to the expanded slit.

FIG. 1 illustrates an example pill dispensing device including an upper portion, a circuit board printed on a lower portion, and a pill package, arranged in accordance with at least some examples as described herein.

In a system according to examples, a pill dispensing device may enable tracking pill removal from a pill package 110, such as a blister pack. An example pill dispensing device may include an upper portion 100 and a lower portion 150, which may act as a housing for the pill package 110. The pill package 110 may include one or more pockets or cavities 102, where each cavity 102 may contain a pill or tablet for consumption by a patient. The cavities 102 may be sufficiently collapsible to enable a pill to be dispensed by an application of pressure to the cavity 102 by pressing or pushing the cavity 102. The pill package 110 may have a backing composed from a breakable paper, foil, and/or plastic to enable the pill to break the backing when pushed out of the cutouts and/or openings.

In an example, the upper portion 100 may include cutouts 124 and/or openings corresponding to locations of the cavities 102 of the pill package 10 when the pill package 110 is inserted and aligned with the upper portion 100. The cutouts 124 and/or openings may provide access to the cavities 102 of the pill package 110 to enable dispensing of a pill by pushing one or more of the cutouts 124 and/or openings.

The upper portion 100 may be configured to accommodate insertion of the pill package 110 and the lower portion 150 within the upper portion 100 to form the pill dispensing device. In other examples, the cavities 102 may also be closed cavities corresponding to the location of the cutouts 124 and/or openings of the pill package 110. The cutouts 124 and/or openings of the upper portion 100 may be thermoformed into the material of the upper portion 100.

In some examples, the lower portion 150 may include a circuit board 130 which may be sandwiched between a top plate 120 and a bottom plate 140 to provide support and protection for the circuit board 130. The top plate 120 and the bottom plate 140 may be composed from a polymer material such as Polyethylene (PE), High Density Polyethylene (HDPE), Polypropylene (PP), Polyethylene Terephthalate (PET), among others. The top plate 120 may include may include a plurality of cutouts 122 and/or openings corresponding to locations of the cavities 102 of the pill package 110 when the pill package 110 is inserted within the pill dispensing device and aligned with the upper portion 100 and the lower portion 150. Likewise, the bottom plate 140 may also include a plurality of cutouts 142 and/or openings corresponding to locations of the cavities 102 of the pill package 110 when the pill package 110 is inserted within the pill dispensing device. The top plate cutouts 122 and the bottom plate cutouts 142 may provide enable dispensing of a pill out of the pill dispensing device.

Additional materials for the top plate 120 and the bottom plate 140 may include paper boards and/or metals. The paper boards and/or metals may offer rigidity for reinforcing and protecting the enclosed circuit board 130. The circuit board 130 may be printed on a composite sheet. The composite sheet may include one or more partially rigid portions, partially flexible portions, and flexible portions. The composite sheet may include slits 132 corresponding to a location of the cavities 102 of the pill package 110 and the cutouts 124 and/or openings of the upper portion 100. The slits 132 may function to detect pill removal from the pill package 110 when a pill is dispensed from a cavity and pushed through a corresponding slit 132. The slits 132 may also be aligned with the top plate cutouts 122 and the bottom plate cutouts 142 when the lower portion 150 is inserted within the upper portion 100 to assemble the pill dispensing device. A pill may be dispensed from the pill package by accessing the cavities 102 through the cutouts 124 of the upper portion, and pushing the pill through the top plate cutouts 122, through a slit of the composite sheet, and through the bottom plate cutouts 142.

In an example, the composite sheet may be at least partially stretchable. For example, the portion of the composite sheet where the slits 132 may be formed may be composed from a stretchable material to enable the slits 132 to expand and contract when a pill may be pushed through a slit 132 while enabling the circuit board 130 to remain conductive when in a stretched form. The composite sheet may be a plastic, a fabric, and/or a silicon-insulator-silicon substrate material, polydimethylsiloxane (PDMS), an elastic PDMS substrate, polyurethane (PU), urethane, polyurethane elastomers, hydrocarbon rubber, hydrocarbon elastomers, polyether block amides (PEBA), nanotube composites, among others.

The circuit board 130 may be printed on the composite sheet such that an individual circuit may correspond to each slit 132 on the composite sheet. The circuit board 130 may be printed employing a lithographic technique, or other similar technique for printing circuits on a reusable material. Similar techniques for printing the circuits on a reusable material may include, among others, subtractive printing and wet etching. An additive printing process may use conductive inks, where the printing process may use, among others, flexographic printing, screen printing, and inkjet offset. In examples, liquid injection molding (LIM) may be used to apply the circuit board 130 to the composite sheet, where the composite sheet may be at least partially stretchable. The slits 132 corresponding to the locations of the pill containing cavities of the pill package may be formed by processes including, among others, laser cutting and die cutting.

A pair of electrical contacts 134 may be incorporated with each individual circuit corresponding to the slit 132 to facilitate detection of pill removal through the slit 132. The electrical contacts 134 may indicate a pill removal through one of detection of a broken circuit or detection of a completed circuit as will be described in further detail below. Each of the individual circuits corresponding to the slits 132 may be connected at a circuitry component of the lower portion 150 such that the circuit may be connected to the main circuit.

The circuitry component may be housed on main circuitry 138 of the composite sheet of the lower portion 150. In examples, the circuitry component may include individual circuits 136 on the main circuitry 138. The main circuitry 138 may also include additional components associated with the circuit board 130, such as a processing unit and/or a controller, a data storage component, and communication components.

In an example, the controller of the main circuitry 138 may be configured to detect the broken circuits and/or closed circuits in response to dispensing a pill through the slits 132 to track pill removal events. The controller may store a record of detected pill removal events at a data store component. The controller may also report the record of removal events to an external monitoring service, such as a healthcare service or pharmaceutical service, for example. The controller may be configured to communicate with the external monitoring service through a communication component. Example communication components may enable a wired communication, a cellular wireless communication, an optical communication, a near field communication, a wireless local area network communication, and a wide area network communication with the external monitoring service.

A composite sheet cording to example embodiments may be manufactured through various methods or combinations thereof known in to those skilled in the art. Similarly, a combination of one or more methods may be employed to print or embed electronic circuits on or into the composite sheet.

Figure 2A:
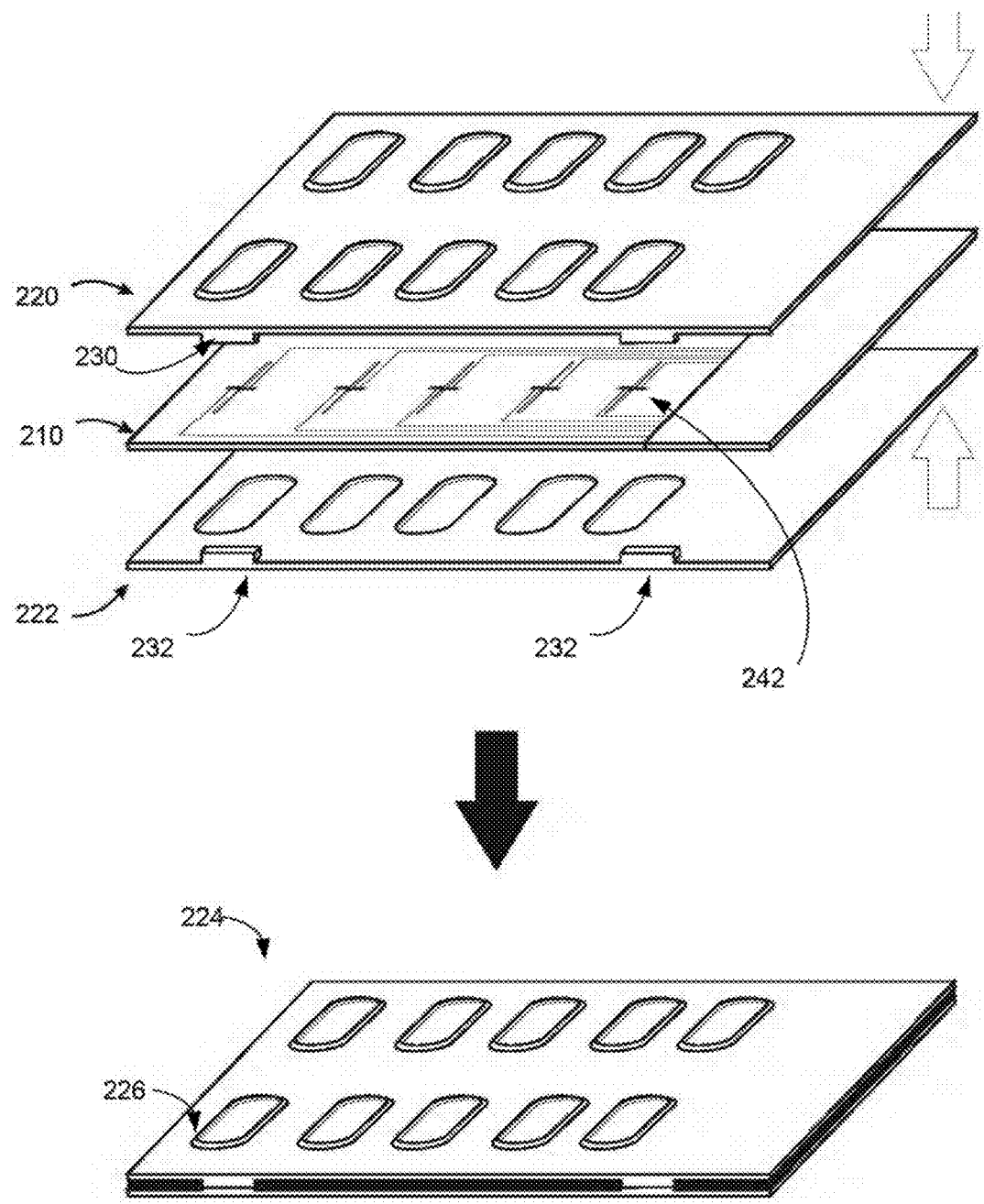
FIGS. 2A, 2B, and 2C illustrate example assemblies of a pill dispensing device.
Figure 2B:
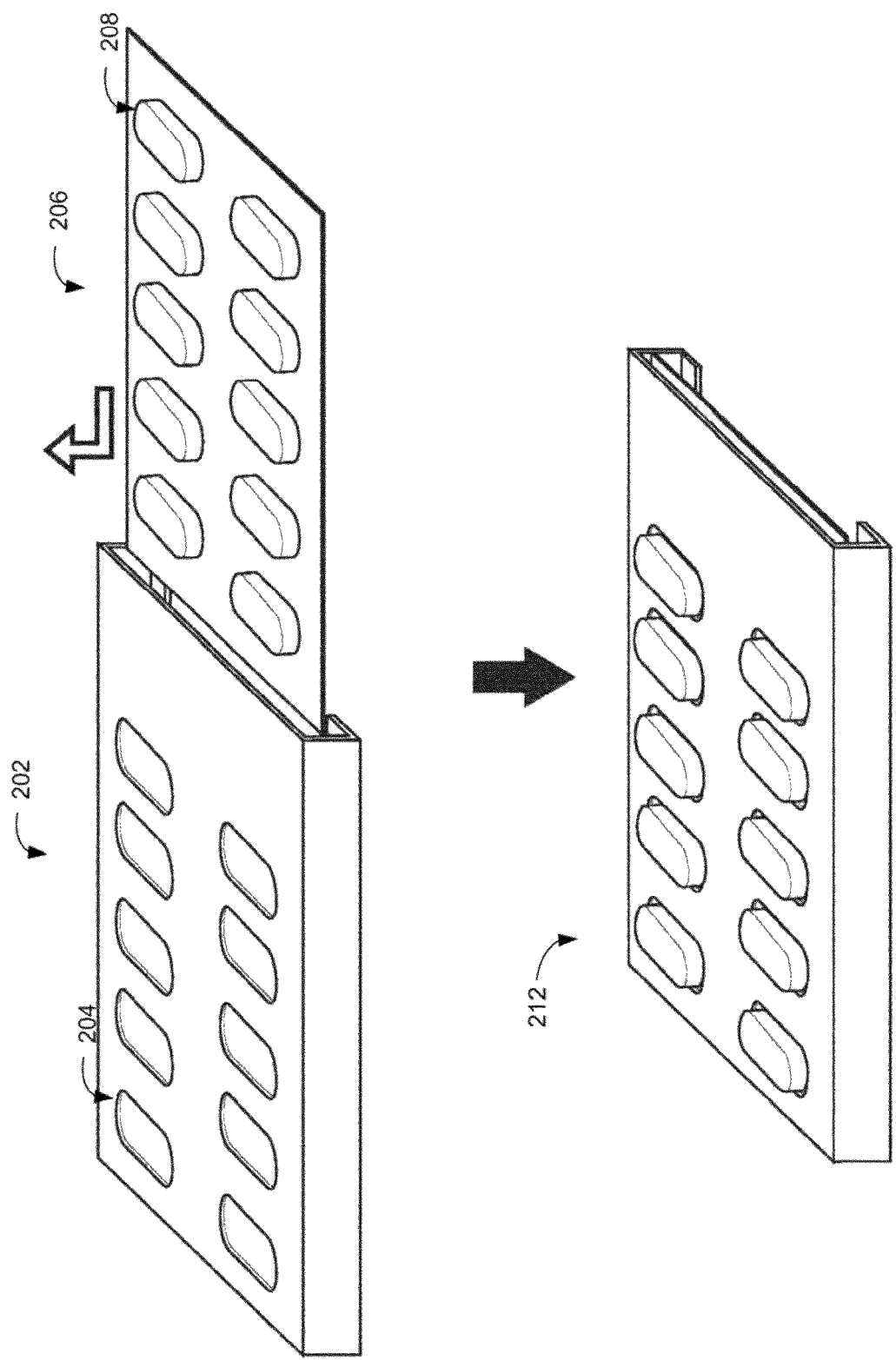
Figure 2C:
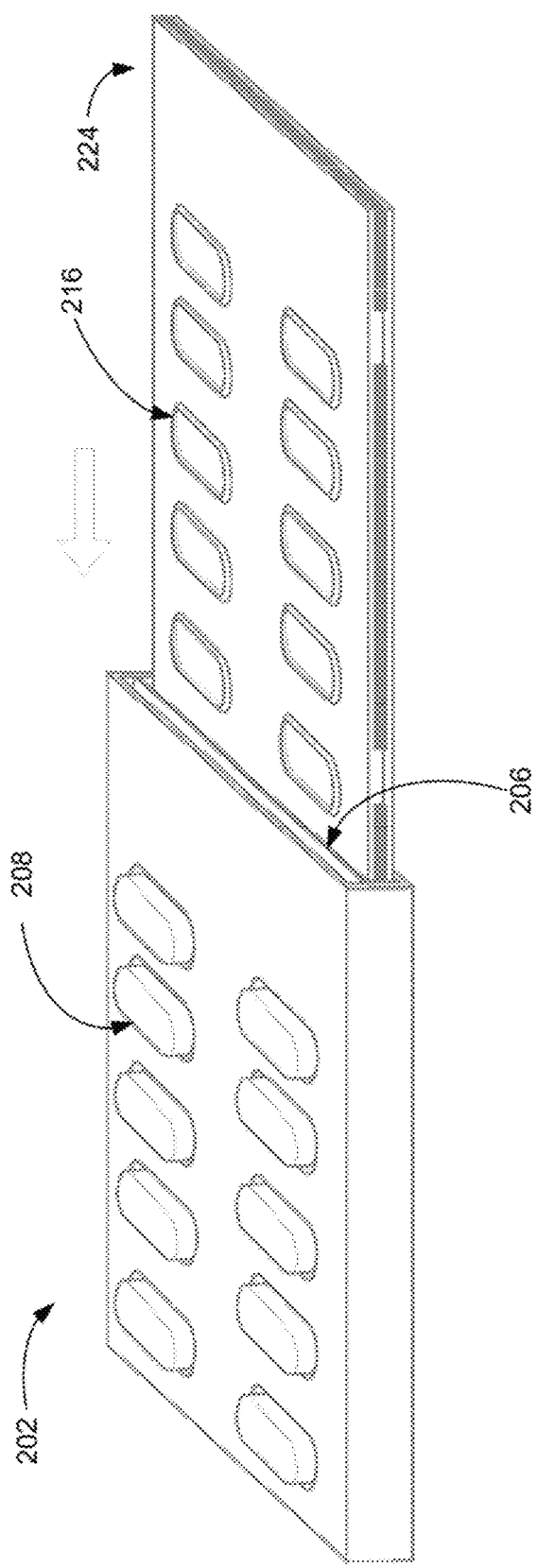

FIGS. 2A, 2B, and 2C illustrate example assemblies of a pill dispensing device, arranged in accordance with at least some examples as described herein.

As described herein, a pill dispensing device may include an upper portion configured to accommodate insertion of a pill package and a lower portion 224, which together with the upper portion may enclose the pill package. In an example, the lower portion 224 may include a circuit board 210 sandwiched between upper and lower plates (e.g., a top plate 220 and a bottom plate 222).

Assembly of the pill dispensing device may include a first step of sandwiching of the circuit board 210, the top plate 220, and the bottom plate 222, as illustrated in FIG. 2A. The top plate 220 and the bottom plate 222 may include attachment features (e.g., 230 and 232) configured to connect or interlock the top plate 220 with the bottom plate 222. The interlocking assembly of the top plate 220 with the bottom plate 222 may be tamper evident and may be configured to be disassembled at an authorized production facility in order to ensure the circuit board is not tampered with.

The top plate 220 and the bottom plate 222 may be composed from a rigid material, and may be configured to reinforce and protect flexible and rigid circuit components from damage during use. The top plate 220 and the bottom plate 222 may also include openings 226 corresponding to slits 242 formed in the circuit board 210. In examples, one or more cutouts may be formed on each side of each slit 242 within flexible portions of the circuit board 210 to facilitate detection of pill removal through the slits 242.

In examples, a pair of electrical contacts may be incorporated with each of the cutouts on one or both sides of each of the slits 242 in order to facilitate detection of removal of a pill from the pill package when the pill is dispensed and pushed through the slits 242. The rigid protective nature of the upper and bottom plates may ensure controlled and predictable behavior of the circuit board in localized zones around the slits 242 where the stretchable characteristic may be desired.

In an example, after assembly of the lower portion 224, an upper portion 202 may be incorporated with the lower portion 224 to form a housing for a pill package 206. As demonstrated in FIG. 2B, a pill package 206 may be inserted into the upper portion 202, such that blisters 208 of the pill package 206 may align with openings 204 formed in the upper portion 202. The pill package 206 may be inserted into the upper portion 202 by sliding the pill package 206 within the upper portion 202 until the blisters 208 align with the openings 204 of the upper portion 202. The assembled upper portion and pill package together 212 may be incorporated with the lower portion to form a pill dispensing device.

As demonstrated in FIG. 2C, after insertion of the pill package 206 within the upper portion, the assembled lower portion 224 may be incorporated with the upper portion 202 to form the housing for the pill package 206. The lower portion 224 may be inserted into the upper portion 202 beneath the pill package 206, such that openings 216 of the lower portion 224 may also align with the blisters 208 of the pill package 206. In some examples, the lower portion 224 and the upper portion 202 may be connected together by sliding the lower portion 224 within the upper portion 202. When the lower portion 224 and the upper portion 202 have been connected together, an assembled pill dispensing device may be formed.

FIG. 3 illustrates a sectional view of an assembled pill dispensing device, arranged in accordance with at least some examples as described herein.

A top view 310 may illustrate a pill 314 in reference to corresponding slits 312 of a composite sheet 332 on which a circuit board is formed. The composite sheet may include the slits 312 corresponding to locations of pill containing cavities of a pill package. The circuit board may also include multiple circuits corresponding to the slits 312 to detect removal of the pill 314 from each pill cavity of the pill package. Each slit 312 may include one or more electrical contacts 316 configured to be in contact with each other when the slit 312 is closed, which may maintain a corresponding circuit in an active state. A change in the state of the circuit from the active state to an inactive state may occur in response to removal of the pill 314 through the slit 312.

A sectional view 320 of an assembled pill dispensing device is illustrated. In examples, the sectional view 320 may include an upper portion 324, a pill package 326, a lower portion, electrical contacts 336, and a pill 322. The lower portion may include, for example, a top plate 328, the composite sheet including the circuit board, and a bottom plate 334, among others. The circuit board formed on the composite sheet 332 may include multiple circuits corresponding to the slits 312 to detect removal of the pill 322 from each pill cavity of the pill package. Each slit 312 may include the electrical contacts 336 configured to be in contact with each other when the slit 312 is closed to maintain an active state for each circuit corresponding to the slit 312. A change in the state of the circuit from the active state to an inactive state may occur in response to removal of the pill 314 through the slit 312.

Figure 4:
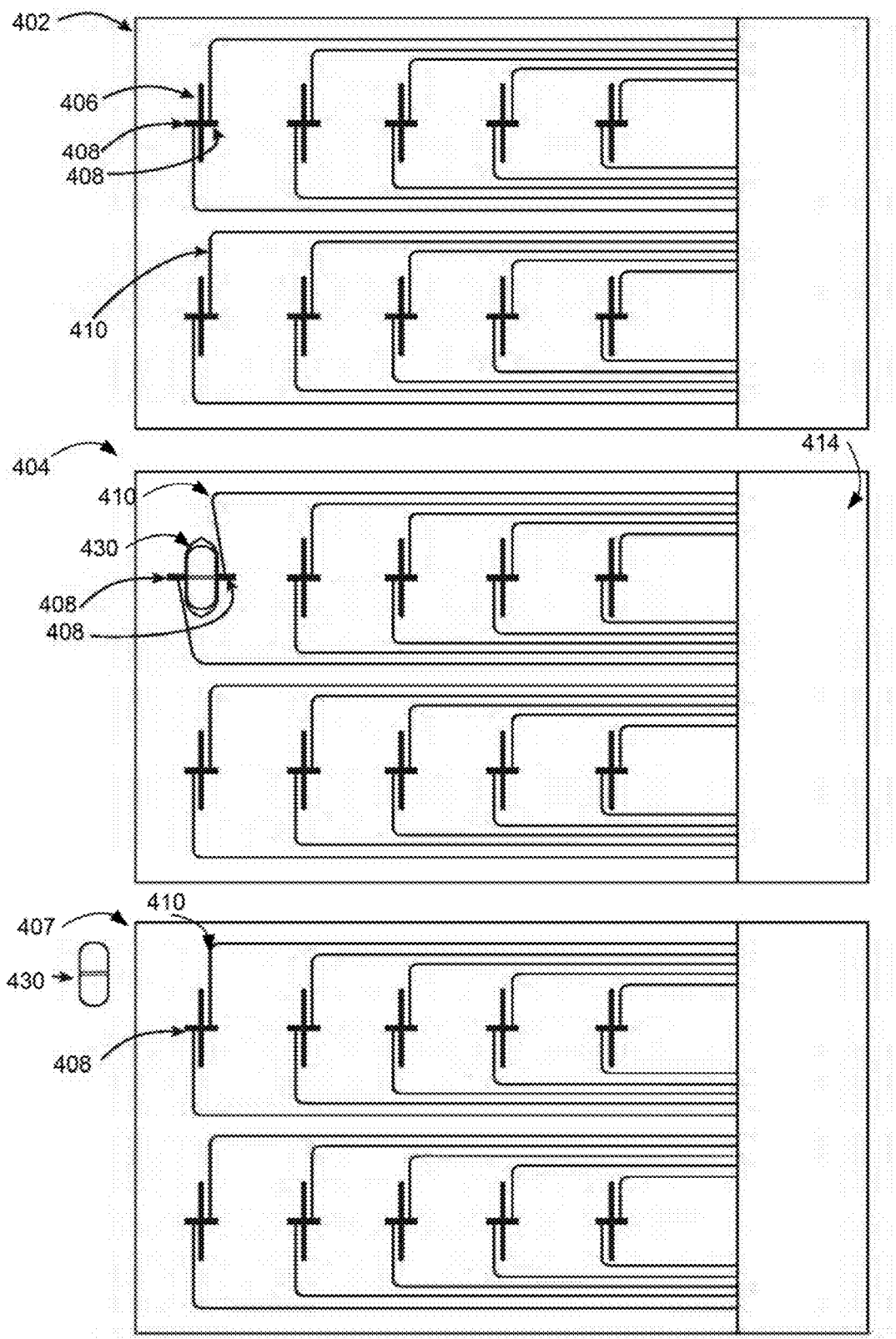
FIG. 4 illustrates example removal of a pill through a slit of a circuit board in a default closed circuit configuration.

FIG. 4 illustrates example removal of a pill through a slit of a circuit board in a default closed circuit configuration, arranged in accordance with at least some examples as described herein.

In an example, as described herein, slits 406 corresponding to locations of pill containing cavities of a pill package may be formed on composite sheet. The composite sheet may include one or more partially rigid portions, partially flexible portions, and flexible portions. The composite sheet may include the slits 406 corresponding to locations of pill containing cavities and/or openings of the pill package. A circuit board including individual circuits may be printed onto the composite sheet, such that an individual circuit 410 may correspond to each slit 406.

As illustrated in a configuration 402, a pair of electrical contacts 408 may be incorporated with each slit 406 to complete the individual circuit 410 corresponding to each slit 406 on the circuit board. The electrical contacts 408 may be configured to be in contact with each other when each slit 406 is in a default closed configuration in order to maintain a closed or active state for the individual circuit 410 corresponding to the slit 406. A change in the state of the circuit from the default active state to an inactive state may occur in response to removal of a pill 430.

As illustrated in a configuration 404, when the slit 406 is expanded in response to dispensing of the pill 430 through the slit 406, the electrical contacts 408 may separate, and the individual circuit 410 corresponding to the expanded slit 406 and separated contacts may be broken. The broken circuit may indicate the removal of the pill 430.

As illustrated in a configuration 407, when the pill 430 is removed from the pill dispensing device through the slit 406, the slit 406 may return to its default closed configuration, and the pair of electrical contacts 408 may re-connect to close the individual circuit 410 and restore the individual circuit 410. In examples, a change in the state of the circuit from the default active state to an inactive state may occur in response to removal of the pill 430. In some examples, the individual circuits corresponding to each of the slits 406 may be configured to be active only when a pill removal event is occurring in order to conserve power by keeping the circuit on a low power consuming mode. The circuit(s) may be powered on in response to a trigger event, which may be an initial stretch of the slit 406 due to an initially pushing of the pill 430 through the slit 406. The individual circuit may remain active for a limited period of time. If the pill 430 is removed through the slit, then the circuit may be broken and made inactive, and the power mode may be returned to a low or zero consuming mode.

As previously described, a processing unit such as a controller component of the circuit board, which may be housed on rigid portions 414 of the composite sheet, may detect the broken circuit to detect the pill removal. The controller component may interpret the detected broken circuit to identify a specific location of pill removal from the pill package. Additionally, a time instance of the broken circuit may be recorded to log a time of removal of the corresponding pill 430. A record of removal events including a time and specific location may be stored locally by the controller in a data store component of the rigid portions 414 of the composite sheet. Additionally, the record of removal events may be communicated to other external devices via various communication protocols as described herein. The record of pill removal events including the pill removal data may be further interpreted and analyzed by third parties to assess patient compliance and to generate further compliance recommendations and information useful for a medical practitioner(s) and/or pharmaceutical companies, for example.

Figure 5:
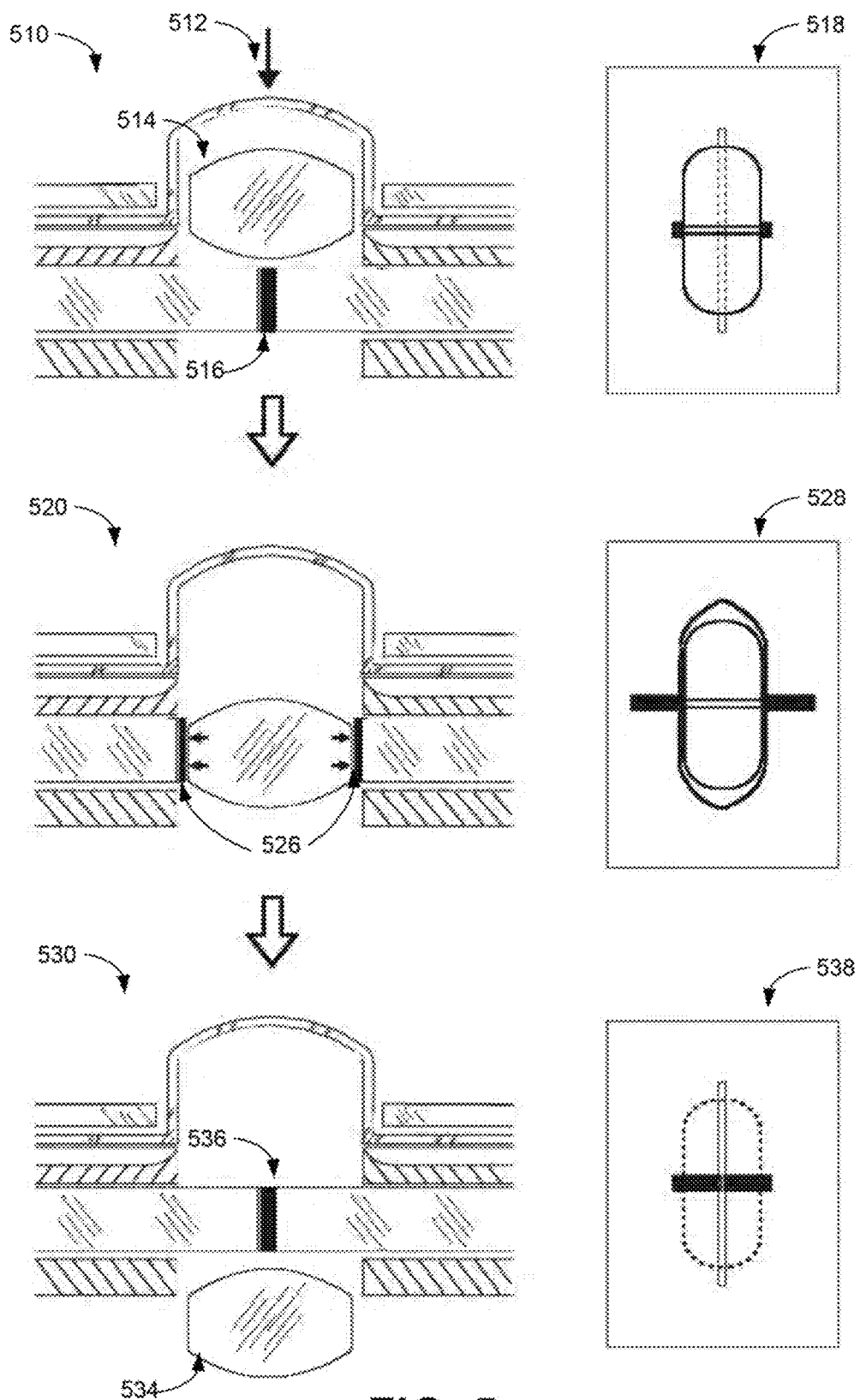
FIG. 5 illustrates a first example of a pill expanding a slit to separate contacts and break a circuit and a second example of the pill closing the slit to restore the circuit to an active state.

FIG. 5 illustrates a first example of a pill expanding a slit to separate contacts and break a circuit and a second example of the pill closing the slit to restore the circuit to an active state, arranged in accordance with at least some examples as described herein.

In a sectional view 510 of the assembled pill dispensing device, a cross section of a circuit board may be shown. The circuit board may include multiple circuits corresponding to the slits to detect removal of a pill 514 from each pill cavity of the assembled pill dispensing device. Each slit may include electrical contacts 516 configured to be in contact with each other when the slit is closed to maintain an active state. In examples, a change in the state of the circuit from the active state to an inactive state may occur in response to removal of the pill 514. In examples, the pill 514 may be pressed against the electrical contacts 516, in response to a compression of a blister 512 of the pill package. A sectional-top view 518 of the assembled pill dispensing device is illustrated, where the pill 514 is shown as larger than the slit and resting above the composite board.

In response to the compression of the blister 512 of the pill package, the pill 514 may be pressed against the electrical contacts 516. In a sectional view 520, the pill 514 may force the slit containing the electrical contacts 516 to expand 526. Configuration 528 illustrates a top view of the pill 514 expanding the slit containing the electrical contacts 516, which may separate the electrical contacts 516. In this example, the broken circuit may indicate a pill removal event. The device may store a record of the pill removal event.

Configuration 530 illustrates a sectional view of a closure of the slit containing the electrical contacts 516, which may allow the slit containing the electrical contacts 516 to be in contact with each other to restore the connection of the circuit corresponding to the slit. In this example, an active state may be maintained for each circuit corresponding to the slit containing the electrical contacts 536. A change in the state of the circuit from the active state to an inactive state may occur in response to removal of the pill. The pill 534 may be dispensed from the device, separating the contacts to break the circuit corresponding to the slit and causing a pill removal event to be recorded in response to the broken circuit. Configuration 538 illustrates a top view of the slit closing to restore the circuit to its active state.

The term "expand" is used herein to describe the change in the slit when a pill is pushed through it. The term "expand" may include, but is not limited to, stretch, open, flex, deform, change shape, etc.

Figure 6:
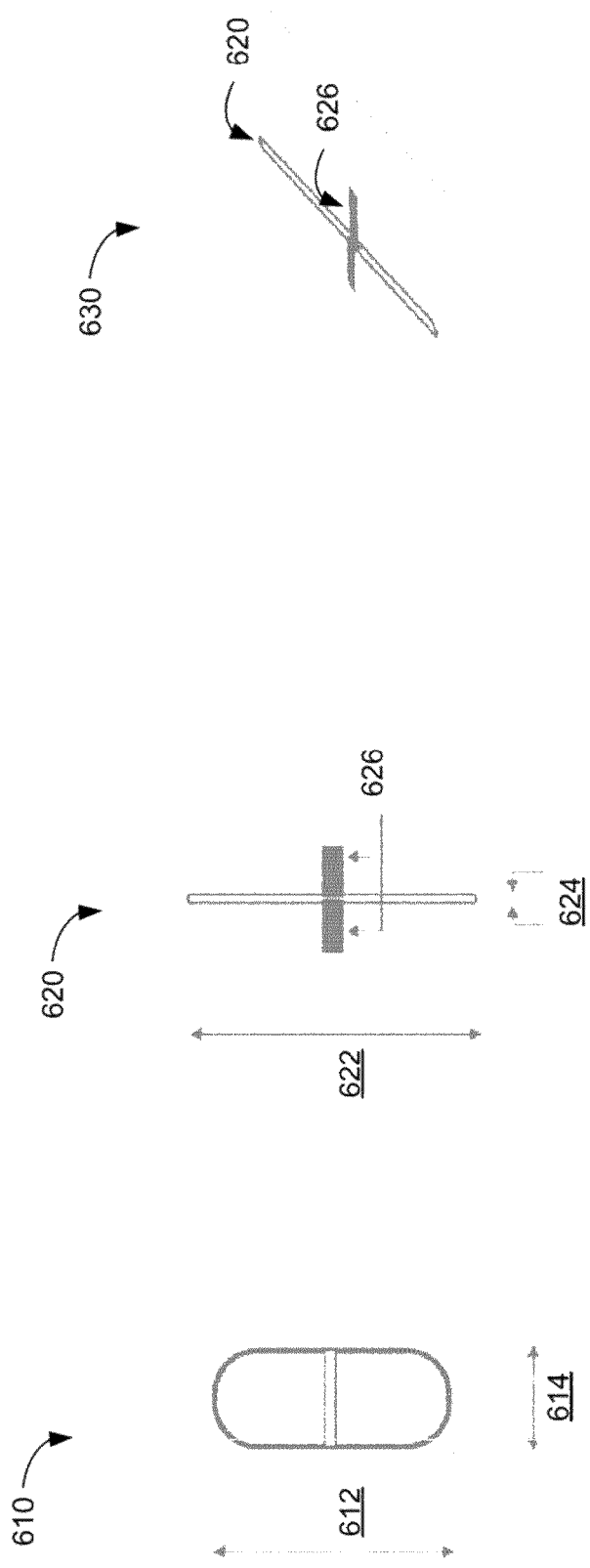
FIG. 6 illustrates a relationship between a pill and slit dimensions of a circuit board.

FIG. 6 illustrates a relationship between a pill and slit dimensions of a circuit board, arranged in accordance with at least some examples as described herein.

A configuration 610 may illustrate pill major dimensions 612 and pill minor dimensions 614 of a pill. A configuration 620 may illustrate slit major dimensions 622, slit minor dimensions 624, and electrical contacts 626. Each slit may include the electrical contacts 626, which may be configured to be in contact with each other when the slit is closed to maintain an active state for each circuit corresponding to the slit. In examples, a change in the state of the circuit from the active state to an inactive state may occur in response to removal of the pill.

In examples, the slit major dimension 622 is greater than the pill major dimension 612. Additionally, the slit minor dimension 624 is lesser than the pill minor dimension 614. In some examples, the slit major dimension 622 may be less than the pill major dimension 612. Additionally, in some examples, the slit minor dimension 624 may be less than the pill minor dimension 614. In further examples, the slit major dimension 622 may be equal to the pill major dimension 612. In additional examples, the slit minor dimension 624 may be equal to the pill minor dimension.

A configuration 630 may illustrate a three-dimensional view of a slit 620 and electrical contacts 626. The composite sheet may include the slit 620 corresponding to locations of the pill containing cavities and/or openings of the pill package.

Figure 7:
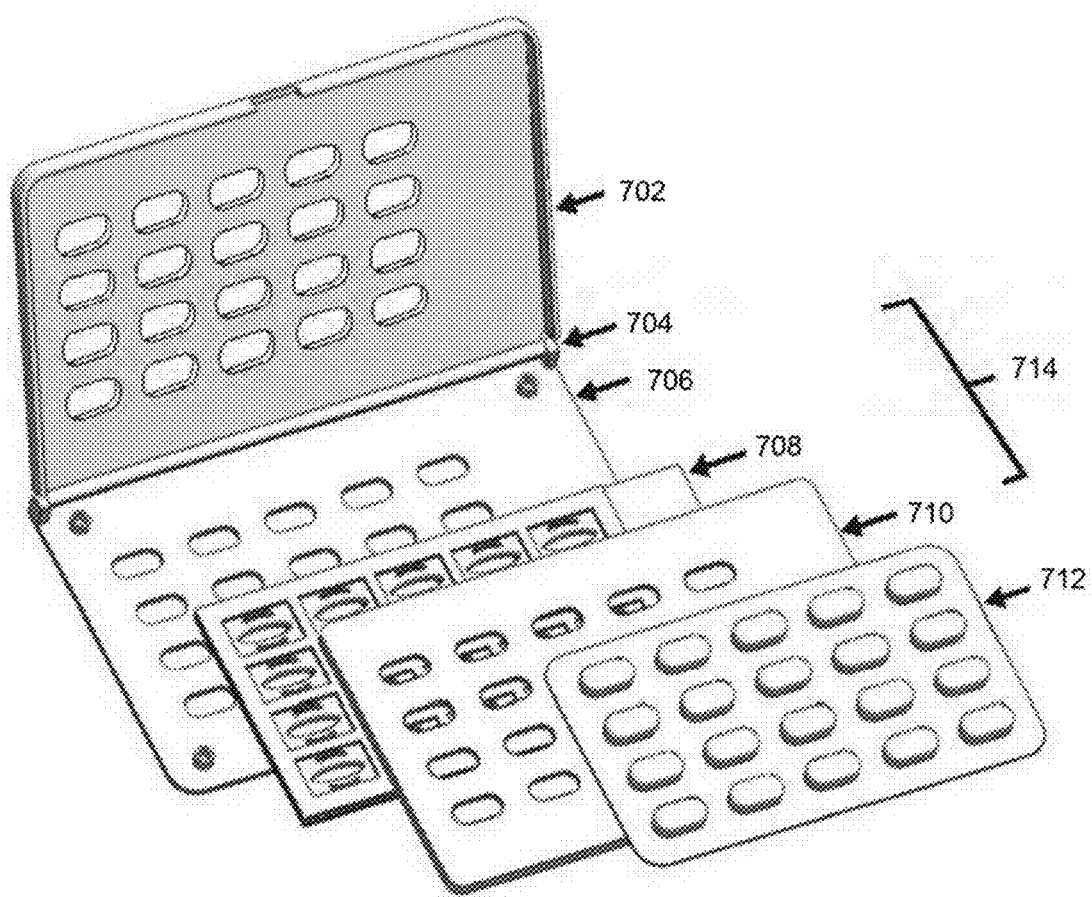
FIG. 7 illustrates an alternative exploded view of an assembled pill dispensing device.

FIG. 7 illustrates an alternative exploded view of an assembled pill dispensing device, arranged in accordance with at least some examples as described herein.

In some examples, the assembled pill dispensing device may include an upper portion 702, a lower portion 714, a pill package 712, and a hinge 704. The lower portion may include, among other things, a bottom plate 706, a circuit board 708, and a top plate 710. The hinge 704 may connect the lower portion 714 with the upper portion 702, in examples.

In some examples, the hinge 704 may be located at an edge of the lower portion 714 and the upper portion 702. Other connecting mechanisms may also be employed to connect the lower portion 714 and the upper portion 702 in order to encase the pill package 712 within the lower portion 714 and the upper portion 702. In some examples, a fastening or locking mechanism may also be employed to enable the upper portion 702 and the lower portion 714 to fasten together to enclose the pill package 712 without allowing the pill dispensing device to inadvertently open. When all pills are removed from the pill package 712, the upper portion 702 and the lower portion 714 may be opened to remove the used pill package 712 and a new pill package may be inserted.

The pill package 712 may be inserted within the lower portion 714 and the upper portion 702 by sliding the pill package 712 between the lower portion 714 and the upper portion 702, or by placing the pill package 712 between the hinged lower portion and the upper portion and closing the upper portion 702 and the lower portion 714.

FIG. 8 illustrates an assembled section view of an assembled pill dispensing device, arranged in accordance with at least some examples as described herein.

In examples, a sectional view of an assembled pill dispensing device is illustrated. In examples, the sectional view may include an upper portion 804, a pill package 806, a lower portion 820, electrical contacts 818, and a pill 802, among other elements. The lower portion 820 may include, for example, a top plate 808, a circuit board 814, and a bottom plate 816, among other features. The circuit board 814 may include, among other things, rigid portions 810 and flexible portions 812. The rigid portions 810 and the flexible portions 812 may be partially rigid and/or partially flexible. One or more slits 830 may be formed in the circuit board 814 to enable the pill 802 to be dispensed through the slit 830. Additionally, cutouts 822 may be formed in the circuit board on each side of each slit 830.

The circuit board 814 may include multiple circuits corresponding to the slits to detect removal of the pill 802 from each pill cavity of the pill package 806. Each cutout 822 on each side of the slit 830 may include the electrical contacts 818. In some examples, the electrical contacts 818 may be configured to be separated from with each other when the slit 830 is closed to maintain an inactive state for each circuit corresponding to the slit 830. When the pill 802 is removed from the pack, the slit 830 may expand and may cause the cutouts 822 on each side of the slit 830 to compress together. When the cutouts 822 compress, the electrical contacts 818 may come into contact with each other, closing the circuit corresponding to the expanded slit 830. Closing the circuit changes the state of the circuit from an inactive state to an active state. The change in the state of the circuit from the inactive state to an active state may occur in response to removal of the pill 802, and may indicate a pill removal event.

Figure 9A:
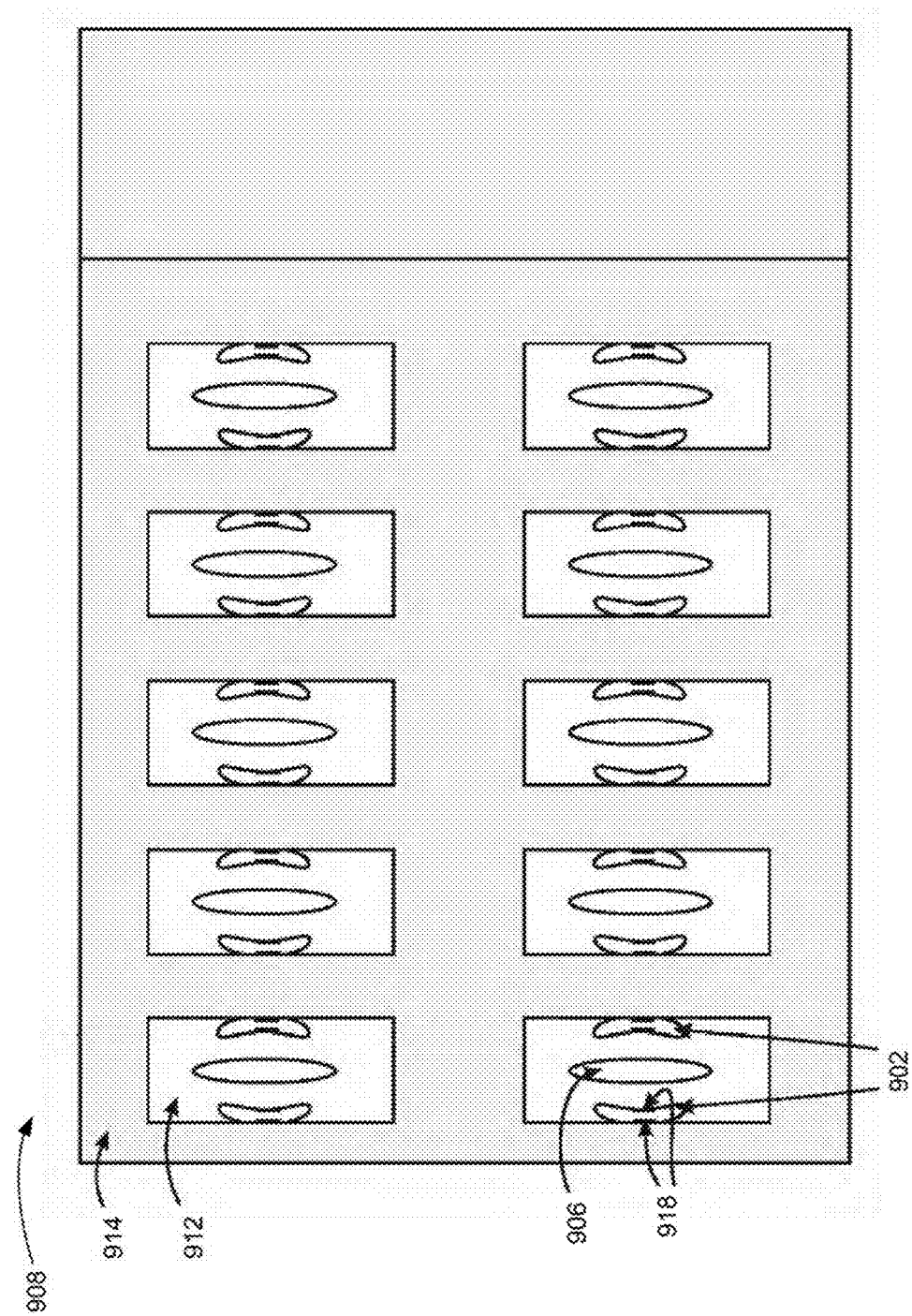
FIGS. 9A and 9B illustrates construction of a circuit board with individual circuits.
Figure 9B:
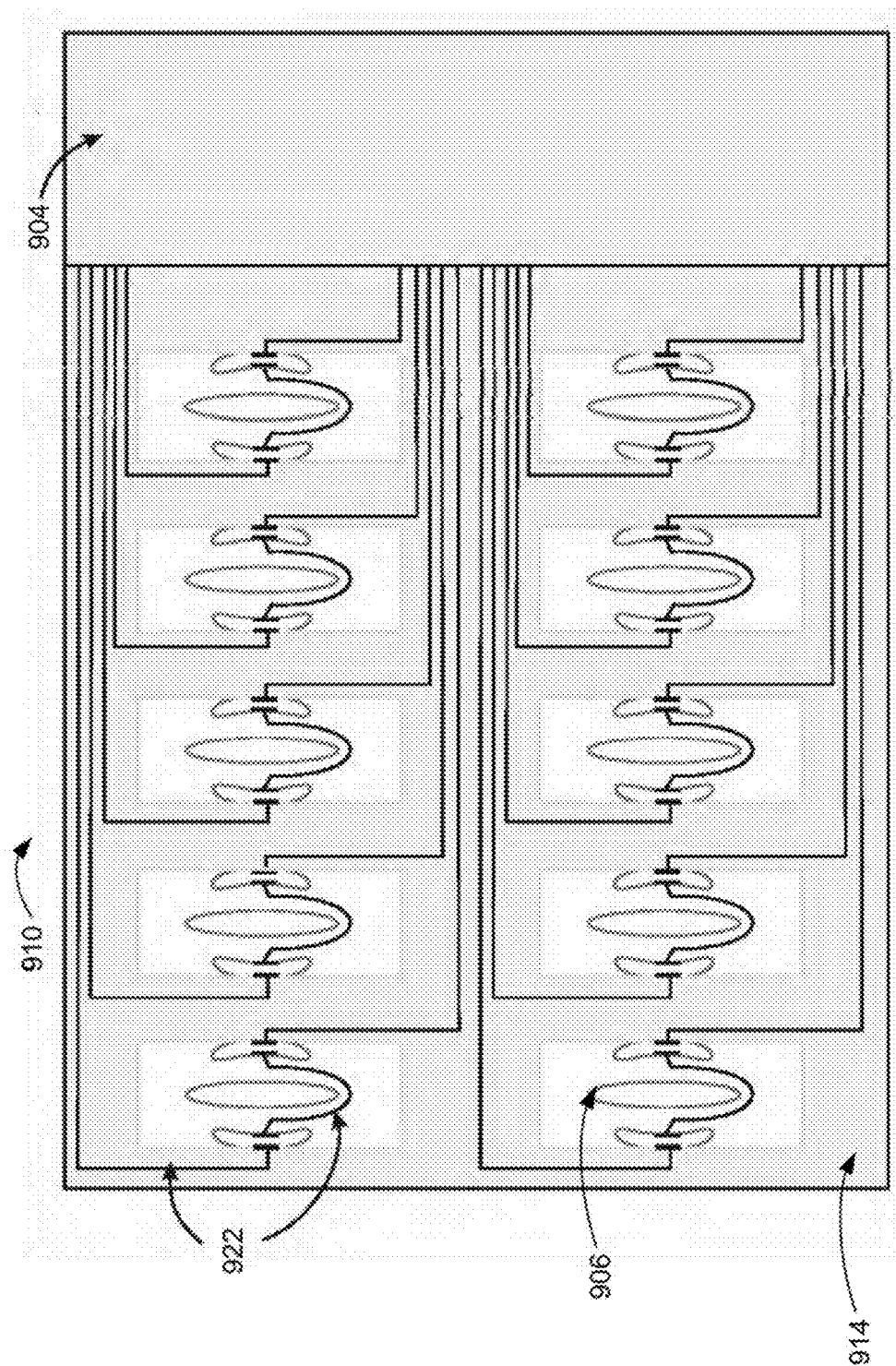

FIGS. 9A and 9B illustrate construction of a circuit board with individual circuits, arranged in accordance with at least some examples as described herein.

In another example, as demonstrated in FIGS. 9A and 9B, a circuit board construction with an individual circuit corresponding to a location of a pill in a pill package enclosed within a pill dispensing device may be configured such that the individual circuit is in a default inactive state. A change in state of the circuit from the inactive state to an active state in response to removal of a pill may indicate a pill removal event. As previously described herein, slits 906 corresponding to locations of pill containing cavities of a pill package may be formed on a composite sheet 908 which may include flexible portions 912 and rigid portions 914.

As shown in FIG. 9A, in an example embodiment, cutouts 902 may be formed on each side of each slit within the flexible portions 912 of the composite sheet 908. A pair of electrical contacts 918 may be incorporated with each of the cutouts 902 on one or both sides of each of the slits 906 in order to facilitate detection of removal of a pill from the pill package when the pill is dispensed and pushed through the slit. When the pill is dispensed through the slit 906, the slits may expand and may cause the cutouts 902 to compress together, bringing the electrical contacts 918 into contact with each other. When the electrical contacts 918 are in contact with each other, the circuit state may change from the default inactive state to an active state to indicate a pill removal event. In examples, the composite sheet 908 may include the rigid portions 914 and the flexible portions 912, where the flexible portions may be partially flexible. The slits 906 and the cutouts 902 may be formed in the flexible portions 912 of the composite sheet.

As demonstrated in FIG. 9B, in a system according to examples, a circuit board 910 including individual circuits 922 may be printed onto the composite sheet such that the individual circuits 922 may correspond to each of the slits 906, and each individual circuit 922 may be connected to the main circuitry 904 housed on the rigid portions 914. The main circuitry 904 may be depicted adjacent to the individual circuit, but may be located in varying locations.

Figure 10:
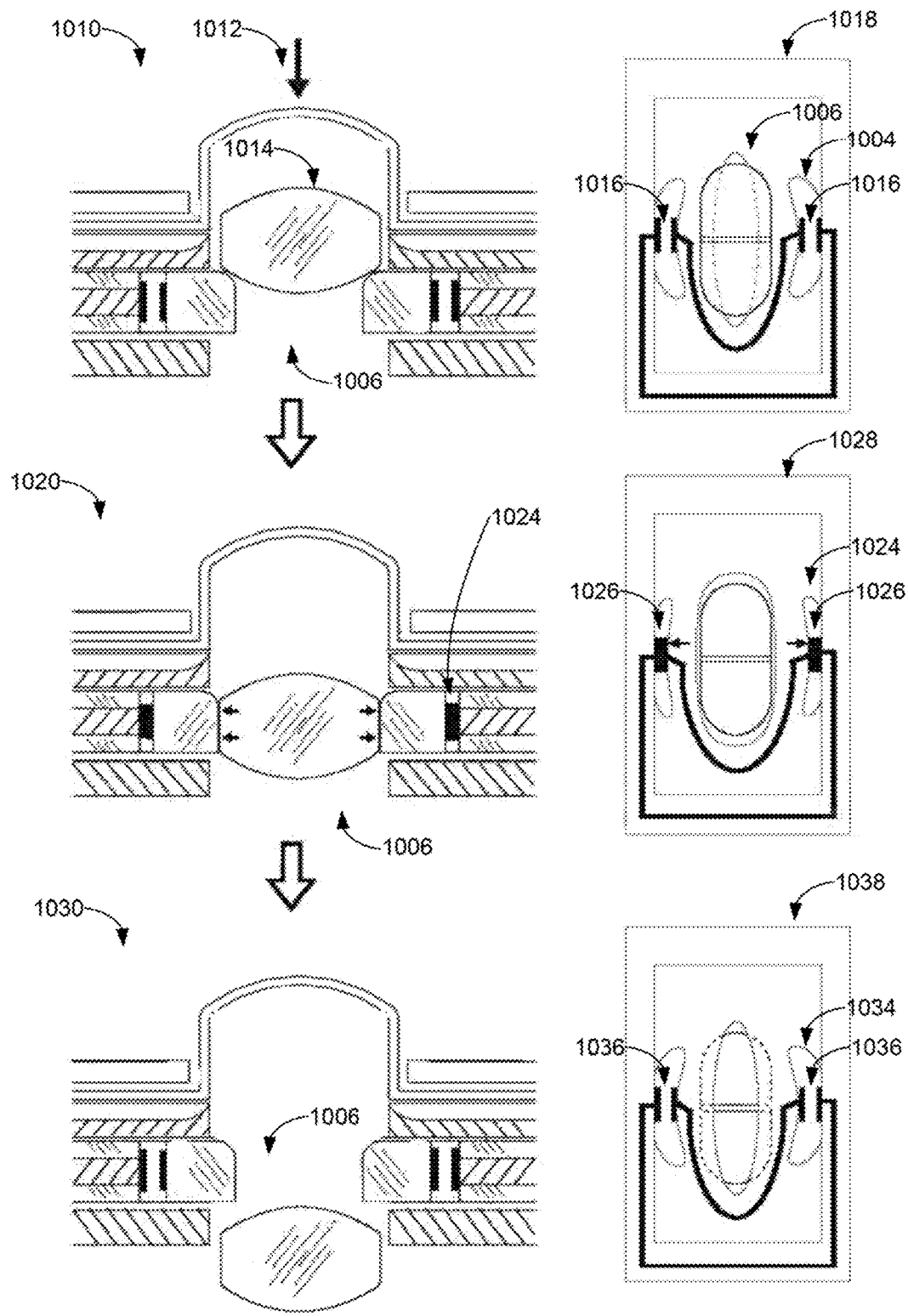
FIG. 10 illustrates a first example of a pill expanding a slit to force electrical contacts against each other to close a circuit and a second example of the pill closing the slit to restore the circuit to an inactive state.

FIG. 10 illustrates a first example of a pill expanding the slit to force electrical contacts against each other to close the circuit and a second example of the pill closing the slit to restore the circuit to an inactive state, arranged in accordance with at least some examples described herein.

In a sectional view 1010 of the assembled pill dispensing device, a circuit board may be shown. The circuit board may include multiple circuits corresponding to slits 1006 to detect removal of a pill 1014 from each pill cavity of the assembled pill dispensing device. A top view 1018 of the sectional view 1010 is illustrated displaying a slit 1006 and corresponding cutouts 1004. Cutouts 1004 may be formed on each side of the slit 1006, and each cutout 1004 may include electrical contacts 1016 configured to be separated from each other when the slit 1006 is closed to maintain an inactive state for each circuit corresponding to the slit 1006. In examples, a change in the state of the circuit from the inactive state to an active state may occur in response to removal of the pill 1014 through the slit 1006. In response to a determination of the compression of the blister 1012 of the pill package, the pill 1014 may be pressed against the slit 1006, in the first example.

In a sectional view 1020, the pill 1014 may force the slit 1006 to expand. The expanded slit 1006 may cause the cutouts 1024 including electrical contacts 1026 to compress brining the electrical contacts 1026 into contact with each other. Configuration 1028 illustrates a top view of the pill 1014 expanding the slit 1006 and compressing the cutouts 1024 containing the electrical contacts 1026, which may compress the electrical contacts 1026 and close the circuit. The closed circuit indicates a change in state from inactive state to active state.

In sectional configuration 1030, the pill 1014 may be removed from the pill package, and the slit 1006 may return to its unexpanded configuration. A pill removal event may occur in response, for example. The device may store a record of the pill removal event. In a top configuration 1038, the slit 1006 may close and the cutouts 1034 containing electrical contacts 1036 may relax to separate the electrical contacts 1035 and restore the circuit to its inactive state, where the inactive state is a default open circuit. In other examples as described herein, however, the active state may be a closed circuit and the inactive state may be an open circuit.

Figure 11:
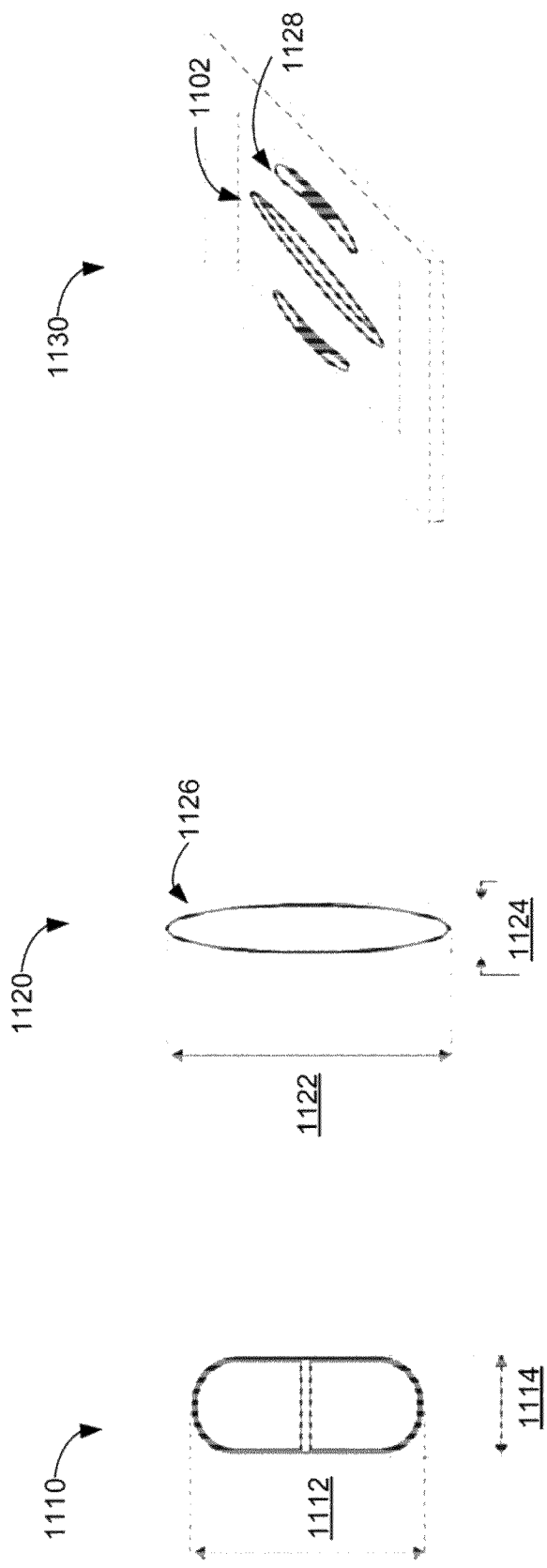
FIG. 11 illustrates a relationship between a pill and slit dimensions of a circuit board.

FIG. 11 illustrates a relationship between a pill and slit dimensions of a circuit board, arranged in accordance with at least some examples described herein.

A configuration 1110 may illustrate pill major dimensions 1112 and pill minor dimensions 1114 of the pill. In a configuration 1120, the composite sheet may include slits 1126 corresponding to locations of pill containing cavities of the pill package. The configuration 1120 may illustrate slit major dimensions 1122 and slit minor dimensions 1124. Each cutout 1128 may include electrical contacts, which may be configured to not be in contact with each other when the slit 1126 is closed to maintain an inactive state for each circuit corresponding to the slit 1126. In examples, a change in the state of the circuit from the inactive state to an active state may occur in response to removal of the pill.

In an example configuration 1130, a three-dimensional view of a slit 1102 may be illustrated with cutouts 1128. In some examples, the cutouts 1128 may include electrical contacts, which may be configured to be separate from other when the slit 1102 is closed to maintain an inactive state for each circuit corresponding to the slit 1102. In examples, a change in the state of the circuit from the inactive state to an active state may occur in response to removal of the pill through the slit 1102.

In examples, the pill package may include pockets or cavities, where each cavity may contain a pill or tablet for consumption by a patient. The cavities may be sufficiently collapsible to enable a pill to be dispensed by applying pressure to the cavity by pressing or pushing the cavity. In examples, the cavities may appear as a cutout with a lip portion.

In some examples, the slit major dimension 1122 may be lesser than the pill major dimension 1112. Additionally, the slit minor dimension 1124 may be greater than the pill minor dimension 1114. In other examples, the slit major dimension 1122 may be less than the pill major dimension 1112. Additionally, in further examples, the slit minor dimension 1124 may be less than the pill minor dimension 1114. In further examples, the slit major dimension 1122 may be equal to the pill major dimension 1112 and the slit minor dimension 1124 may be equal to the pill minor dimension 1114.

Figure 12:
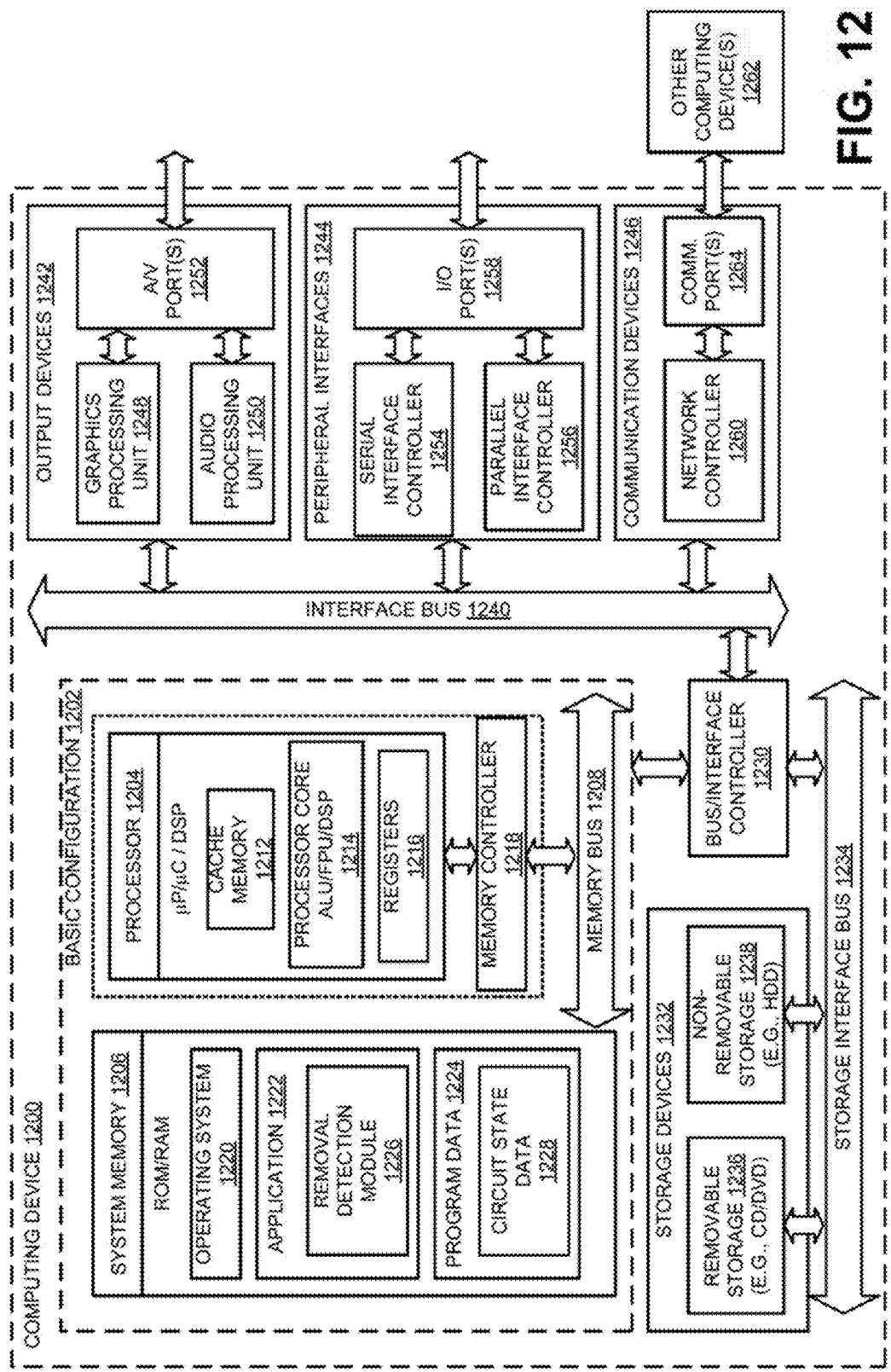
FIG. 12 illustrates a general purpose computing device, which may be used to detect pill removal from a pill package.

FIG. 12 illustrates a general purpose computing device, which may be used to detect pill removal from a pill package, arranged in accordance with at least some examples as described herein.

For example, a computing device 1200 may be used as a server, desktop computer, portable computer, smart phone, special purpose computer, or similar device. In an example basic configuration 1202, the computing device 1200 may include one or more processors 1204 and a system memory 1206. A memory bus 1208 may be used for communicating between the processor 1204 and the system memory 1206. The basic configuration 1202 is illustrated in FIG. 12 by those components within the inner dashed line.

Depending on the desired configuration, the processor 1204 may be of any type, including but not limited to a microprocessor (µP), a microcontroller (µC), a digital signal processor (DSP), or any combination thereof. The processor 1204 may include one more levels of caching, such as a level cache memory 1212, one or more processor cores 1214, and registers 1216. The example processor cores 1214 may (each) include an arithmetic logic unit (ALU), a floating point unit (FPU), a digital signal processing core (DSP Core), or any combination thereof. An example memory controller 1218 may also be used with the processor 1204, or in some implementations, the memory controller 1218 may be an internal part of the processor 1204.

Depending on the desired configuration, the system memory 1206 may be of any type including but not limited to volatile memory (such as RAM), non-volatile memory (such as ROM, flash memory, etc.) or any combination thereof. The system memory 1206 may include an operating system 1220, one or more applications 1222, and program data 1224 such as circuit state data 1228. The application 1222 may include a removal detection module 1226, which may be an integral part of the application 1222 or a separate application on its own.

The removal detection module 1226 may facilitate detection of dispensing of a pill from a pill package enclosed within a pill dispensing device by detecting a change in state of a circuit corresponding to a pill containing cavity of the pill package. The program data 1224 may include, among other data, circuit state data 1228 for individual circuits associated with slits corresponding to each pill containing cavity of the pill package to detect a pill removal event, for example, as described herein. The program data may also be reconfigurable program data that can be reset upon refill of a new pill package.

The computing device 1200 may have additional features or functionality, and additional interfaces to facilitate communications between the basic configuration 1202 and any desired devices and interfaces. For example, a bus/interface controller 1230 may be used to facilitate communications between the basic configuration 1202 and one or more data storage devices 1232 via a storage interface bus 1234. The data storage devices 1232 may be one or more removable storage devices 1236, one or more non-removable storage devices 1238, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 1206, the removable storage devices 1236 and the non-removable storage devices 1238 may be examples of computer storage media. Computer storage media includes, but is not limited to, RAM, ROM, EEPROM, flash memory or other memory technology, CD-ROM, digital versatile disks (DVD), solid state drives, or other optical storage, magnetic cassettes, magnetic tape, magnetic disk storage or other magnetic storage devices, or any other medium which may be used to store the desired information and which may be accessed by the computing device 1200. Any such computer storage media may be part of the computing device 1200.

The computing device 1200 may also include an interface bus 1240 for facilitating communication from various interface devices (for example, one or more output devices 1242, one or more peripheral interfaces 1244, and one or more communication devices 1246) to the basic configuration 1202 via the bus/interface controller 1230. Some of the example output devices 1242 include a graphics processing unit 1248 and an audio processing unit 1250, which may be configured to communicate to various external devices such as a display or speakers via one or more A/V ports 1252. One or more example peripheral interfaces 1244 may include a serial interface controller 1254 or a parallel interface controller 1256, which may be configured to communicate with external devices such as input devices (for example, keyboard, mouse, pen, voice input device, touch input device, etc.) or other peripheral devices (for example, printer, scanner, etc.) via one or more I/O ports 1258. An example communication device 1246 includes a network controller 1260, which may be arranged to facilitate communications with one or more other computing devices over a network communication link via one or more communication ports 1264. The one or more other computing devices 1262 may include servers, client devices, smart appliances, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 1200 may be implemented as a part of a general purpose or specialized server, mainframe, or similar computer that includes any of the above functions. The computing device 1200 may also be implemented as a personal computer including both laptop computer and non-laptop computer configurations.

Example examples may also include methods to monitor pill removal from a pill dispensing device. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other examples, the human interaction can be automated such as by pre-selected criteria that may be machine automated.

Figure 13:
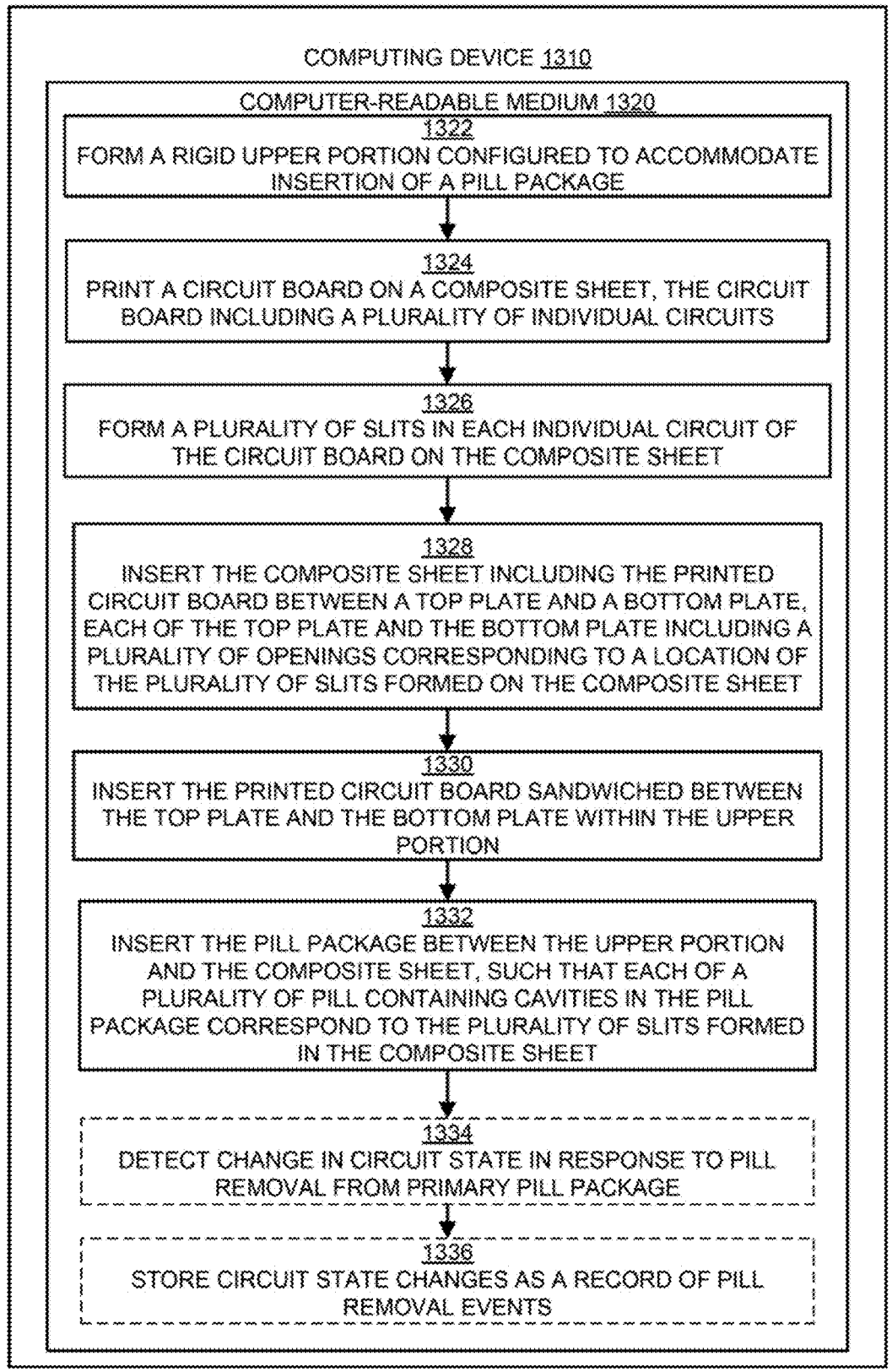
FIG. 13 illustrates a flow diagram, which may describe an example method that may be performed by a computing device such as the computing device in FIG. 12.

FIG. 13 illustrates a flow diagram, which may describe an example method that may be performed by a computing device such as the computing device in FIG. 12, arranged in accordance with at least some examples as described herein.

Example methods may include one or more operations, functions or actions as illustrated by one or more of blocks 1322, 1324, 1326, 1328, 1330, and 1332. The operations described in the blocks 1322 through 1332 may also be stored as computer-executable instructions in a computer-readable medium such as a computer-readable medium 1320 of a computing device 1310. The method may include manufacturing a pill dispensing device to monitor pill removal.

An example process to manufacture the pill dispensing device to monitor the pill removal may begin with block 1322, "FORM A RIGID UPPER PORTION CONFIGURED TO ACCOMMODATE INSERTION OF A PILL PACKAGE," where the upper portion may include openings corresponding to locations of the cavities of the pill package when the pill package is inserted and aligned with the upper portion. The openings may provide access to the cavities of the pill package to enable dispensing of a pill by pushing one or more of the cavities. The upper portion may be configured to accommodate insertion of the pill package and the lower portion within the upper portion to form the pill dispensing device. The dimensions, spacing, and location of upper portion and cavities may be custom-designed to suit the dimensions of a specific pill package to be encased.

Block 1322 may be followed by block 1324, "PRINT A CIRCUIT BOARD ON A COMPOSITE SHEET, THE CIRCUIT BOARD INCLUDING A PLURALITY OF INDIVIDUAL CIRCUITS," where the composite sheet may be a plastic, a fabric, and/or a silicon-insulator-silicon substrate material, polydimethylsiloxane (PDMS), an elastic PDMS substrate, polyurethane (PU), urethane, polyurethane elastomers, hydrocarbon rubber, hydrocarbon elastomers, polyether block amides (PEBA), nanotube composites, among others. The circuit board may be printed on the composite sheet such that an individual circuit may correspond to each slit on the composite sheet. The location of the slit may be custom-designed to suit dimensions of a specific pill package.

The circuit board may be printed employing a lithographic technique, or other similar technique for printing circuits on a reusable material. Similar techniques for printing the circuits on a reusable material may include, among others, subtractive printing and wet etching. An additive printing process may use conductive inks, where the printing process may use, among others, flexographic printing, screen printing, and inkjet offset. In examples, liquid injection molding (LIM) may be used to apply the circuit board to the composite sheet, where the composite sheet may be at least partially stretchable.

Block 1324 may be followed by block 1326, "FORM A PLURALITY OF SLITS IN EACH INDIVIDUAL CIRCUIT OF THE CIRCUIT BOARD ON THE COMPOSITE SHEET," where the slits (e.g. slits 132) corresponding to the locations of the pill containing cavities (e.g. cavities 102) of the pill package may be formed by processes including, among others, laser cutting and dye cutting.

Block 1326 may be followed by block 1328. "INSERT THE COMPOSITE SHEET INCLUDING THE PRINTED CIRCUIT BOARD BETWEEN A TOP PLATE AND A BOTTOM PLATE, EACH OF THE TOP PLATE AND THE BOTTOM PLATE INCLUDING A PLURALITY OF OPENINGS CORRESPONDING TO A LOCATION OF THE PLURALITY OF SLITS FORMED ON THE COMPOSITE SHEET," where the composite sheet including the printed circuit board may be sandwiched between the top plate and the bottom plate. Slits formed in the circuit board may be aligned with openings in the top plate and the bottom plate. Each of the slits may be associated with the individual circuits printed on the circuit board.

Block 1328 may be followed by block 1330, "INSERT THE PRINTED CIRCUIT BOARD SANDWICHED BETWEEN THE TOP PLATE AND THE BOTTOM PLATE WITHIN THE UPPER PORTION," where the lower portion including the printed circuit board sandwiched between the top plate and the bottom plate may be coupled with a rigid upper portion such that openings or cavities of the upper portion may be aligned with the openings formed in the lower portion.

As described herein, a hinge may connect the lower portion with the upper portion. In examples, the hinge may be located at an edge of the lower portion and the upper portion. Other connecting mechanisms may also be employed to connect the lower portion and the upper portion in order to encase the pill package within the lower portion and the upper portion. In some examples, a fastening or locking mechanism may also be employed to enable the upper portion and the lower portion to fasten together to enclose the pill package without allowing the pill dispensing device to inadvertently open. In other examples, the lower portion may be connected together by sliding the lower portion within the upper portion.

Block 1330 may be followed by block 1332, "INSERT THE PILL PACKAGE BETWEEN THE UPPER PORTION AND THE COMPOSITE SHEET, SUCH THAT EACH OF A PLURALITY OF PILL CONTAINING CAVITIES IN THE PILL PACKAGE CORRESPOND TO THE PLURALITY OF SLITS FORMED IN THE COMPOSITE SHEET," where after assembly of the lower portion with the upper portion to form a housing for a pill package, the pill package may be inserted between the upper portion and the lower portion, such that blisters of the pill package may align with openings formed in the upper portion and the lower portion. In some examples, the pill package be inserted by sliding the pill package within the upper portion. When the pill package is inserted between the lower portion and the upper portion, an assembled pill dispensing device may be formed.

In examples, an optional block 1334 may include, "DETECT CHANGE IN CIRCUIT STATE IN RESPONSE TO PILL REMOVAL FROM PRIMARY PILL PACKAGE," where the pill may be dispensed from the pill package and pushed through a corresponding slit of the lower portion. The slit may expand when the pill is pushed through the slit causing the individual circuits associated with the slit to change state. In some examples, the individual circuits associated with the slit may change from an active state to an inactive state. In other examples, the individual circuits associated with the slit may change from the inactive state to the active state. The change in state from the active to the inactive state, or vice versa, may be interpreted as a pill removal event by a controller component associated with the pill dispensing device.

In examples, an optional block 1336 may include, "STORE CIRCUIT STATE CHANGES AS A RECORD OF PILL REMOVAL EVENTS." where a controller component associated with the pill dispensing device may store each changed circuit state as a pill removal event. A record of pill removal events including a time and specific location of a pill removal may be stored in a data store component associated with the pill dispensing device. Additionally, the record of pill removal events may be reported to an external monitoring service.

The blocks included in the above described process are for illustration purposes. Monitoring pill removal from a pill dispensing device may be implemented by similar processes with fewer or additional blocks. In some examples, the blocks may be performed in a different order. In some other examples, various blocks may be eliminated. In other examples, various blocks may be divided into additional blocks, or combined together into fewer blocks.

FIG. 14 illustrates a block diagram of an example computer program product, arranged in accordance with at least some examples described herein.

In some examples, as shown in FIG. 14, the computer program product 1400 may include a signal bearing medium 1402 that may also include one or more machine readable instructions 1404 that, when executed by, for example, a processor may provide the functionality described above with respect to FIG. 12. Thus, for example, referring to the processor 1204 in FIG. 12, the removal detection module 1226 executed on the processor 1204 may undertake one or more of the tasks shown in FIG. 14 in response to the instructions 1404 conveyed to the processor 1204 by the medium 1402 to perform actions associated with monitoring pill removal from a pill dispensing devices described herein. Some of those instructions may include, for example, one or more instructions to form a rigid upper portion configured to accommodate insertion of a pill package, print a circuit board on a composite sheet, the circuit board including a plurality of individual circuits, form a plurality of slits in each individual circuit of the circuit board on the composite sheet, insert the composite sheet including the printed circuit board between a top plate and a bottom plate, each of the top plate and the bottom plate including a plurality of openings corresponding to a location of the plurality of slits formed on the composite sheet, insert the printed circuit board sandwiched between the top plate and the bottom plate within the upper portion, and/or insert the pill package between the upper portion and the composite sheet, such that each of a plurality of pill containing cavities in the pill package correspond to the plurality of slits formed in the composite sheet, according to some examples described herein.

In some implementations, the signal bearing medium 1402 depicted in FIG. 14 may encompass a computer-readable medium 1406, such as, but not limited to, a hard disk drive, a solid state drive, a Compact Disc (CD), a Digital Versatile Disk (DVD), a digital tape, memory, etc. In some implementations, the signal bearing medium 1402 may encompass a recordable medium 1408, such as, but not limited to, memory, read/write (R/W) CDs, R/W DVDs, etc. In some implementations, the signal bearing medium 1402 may encompass a communications medium 1410, such as, but not limited to, a digital and/or an analog communication medium (for example, a fiber optic cable, a waveguide, a wired communications link, a wireless communication link, etc.). Thus, for example, the program product 1400 may be conveyed to one or more modules of the processor 1204 of FIG. 12 by an RF signal bearing medium, where the signal bearing medium 1402 may be conveyed by the wireless communications medium 1410 (for example, a wireless communications medium conforming with the IEEE 802.11 standard).

The present disclosure generally describes an example pill dispensing device. The example pill dispensing device may monitor pill removal. The example pill dispensing device may include, among other things, an upper portion including a plurality of cavities, a lower portion formed from a locally or completely flexible or stretchable composite sheet, and a circuit board printed on or embedded into the composite sheet. The upper portion may be configured to accommodate insertion of a pill package. The composite sheet may include a plurality of slits corresponding to a location of the plurality of cavities of the upper portion. The lower portion may further include a top plate and a bottom plate, where each of the top plate and the bottom plate may include a plurality of openings corresponding to a location of the plurality of slits formed on the composite sheet. The circuit board may include one or more circuits, which may be used to detect removal of pills through the plurality of slits in the composite sheet.

In examples, the plurality of cavities of the upper portion of the pill dispensing device may correspond to a location of one or more pill containing cavities of the pill package. In additional examples, each of the one or more circuits of the pill dispensing device may correspond to each of the plurality of slits of the composite sheet.

In some examples, at least a portion of the composite sheet of the pill dispensing device may include a rigid structural element embedded into the composite sheet such that the composite sheet includes rigid portions and flexible portions. Additionally, each slit may include a pair of electrical contacts configured to be in contact with each other when the slit is closed to maintain a default active closed state for each individual circuit corresponding to the slit. In some examples, the slit is configured to expand in response to removal of a pill from the pill package, causing the pair of electrical contacts to separate and breaking an individual circuit corresponding to the expanded slit and the separated electrical contacts.

In further examples, the broken circuit may indicate a removal of a particular pill from a cavity of the pill dispensing device. Also, in examples, after removal of the pill, the slit may be configured to close following complete removal of the pill and to reconnect the pair of electrical contacts to restore the individual circuit corresponding to the slit to the default active closed state.

In some examples, the pill dispensing device may further include a pair of electrical contacts positioned on one or both sides of each of the plurality of slits, where each of the pair of electrical contacts may be configured to be separated from each other when the slit is closed to maintain a default inactive state for each individual circuit corresponding to the slit and the pair of electrical contacts. The pair of electrical contacts may include one or more cutouts on one or both sides of each of the plurality of slits, where each cutout houses the pair of electrical contacts in a default separated configuration when the slit is closed. In examples, each of the plurality of slits and the one or more cutouts may be formed in flexible portions of the composite sheet.

In further examples, the slit is configured to expand in response to removal of a pill from the pill package, causing the pair of electrical contacts within each cutout to contact each other and closing an individual circuit corresponding to the expanded slit and the electrical contacts. In further examples, the one or more cutouts may be configured to close to bring the electrical contacts in contact with each other when the slit expands. In examples, the closed circuit indicates a removal of a particular pill from a cavity of the pill dispensing device.

In some examples, the slit may be configured to close upon complete removal of the pill from the pill package enabling the pair of electrical contacts to re-separate to restore the individual circuit corresponding to the slit to the default inactive state. A minor dimension of each slit is less than a minor dimension of a pill contained in a corresponding cavity. In examples, a size of each slit is selected to ensure each slit opens when a pill is removed from a cavity.

In further examples, the lower portion includes circuitry configured to connect each individual circuit. In examples, the pill dispensing device may include a controller configured to store a record of each broken circuit detected by the circuitry as a record of removal events. In examples, the circuitry may be connected to the controller via one or more contacts between the upper portion and the lower portion.

In some examples, the controller is configured to report the record of removal events to an external monitoring service. Additionally, the controller may be configured to communicate with the external monitoring service employing one or more of: a wired communication, a cellular wireless communication, an optical communication, a near field communication, a wireless local area network communication, and a wide area network communication.

In examples, each individual circuit may be converted to one or an active state or an inactive state upon detection of a trigger event, where the trigger event is an initial stretch of the slit in response to removal of a pill from a cavity in the pill package. In some examples, the circuit board may be printed on the composite sheet or embedded into the composite sheet through one or more of: a lithographic technique, a subtractive printing technique, a wet etching technique, an additive printing technique, a flexographic printing technique, a screen printing technique, an inkjet offset printing technique, and a liquid injection molding (LIM) technique. The composite sheet, for example, may be formed from one of: a plastic, a fabric, a silicon-insulator-silicon substrate, polydimethylsiloxane (PDMS), an elastic PDMS substrate, polyurethane (PU), urethane, polyurethane elastomers, hydrocarbon rubber, hydrocarbon elastomers, polyether block amides (PEBA), and nanotube composites.

In some examples, the composite sheet may be configured to be reusable with another pill package. The pill package, for example, may be enclosed between the upper portion and the lower portion. In further examples, the lower portion is configured to be removable from the upper portion. In additional examples, the top plate and the bottom plate of the lower portion may be configured to connect together to encase the composite sheet between the top plate and the bottom plate.

The present disclosure also generally describes an example system. The example system may monitor pill removal from a pill dispensing device. The system may include a pill dispensing device, a controller configured to detect a change in a state of the one or more circuits in response to removal of a pill from a cavity of the pill package through the slit in the lower portion, and a remote monitoring service configured to store a record of the removal of the pill from the pill dispensing device. The pill dispensing device may include, at least, an upper portion including a plurality of cavities, a lower portion formed from a locally or completely flexible or stretchable composite sheet, and a circuit board printed or embedded into the composite sheet. The upper portion may be configured to accommodate insertion of a pill package. The composite sheet may include a plurality of slits corresponding to a location of the plurality of cavities of the upper portion. The lower portion may be sandwiched between a top plate and a bottom plate, where each of the top plate and the bottom plate may include a plurality of openings corresponding to a location of the plurality of slits formed on the composite sheet. The circuit board may include one or more circuits to detect removal of pills through the plurality of slits in the composite sheet.

In some examples, the plurality of cavities of the upper portion correspond to a location of one or more pill containing cavities of the pill package. Additionally, each of the one or more circuits corresponds to each of the plurality of slits in the composite sheet. In further examples, each slit includes a pair of electrical contacts configured to be in contact with each other when the slit is closed to maintain a default active state for each individual circuit corresponding to the slit.

In further examples, the controller may be configured to detect the change in the state of the circuit from a default active state to an inactive state in response to separation of a pair of electrical contacts due to an expansion of the slit corresponding to the pill removed from the cavity of the pill package. Additionally, in some examples, one or more pairs of electrical contacts may be positioned on one or both sides of each slit, each pair of electrical contacts configured to be separated from each other when the slit may be closed to maintain a default inactive state for each individual circuit corresponding to the slit and pair of electrical contacts.

In some examples, the controller may be configured to detect the change in the state of the circuit from a default inactive state to an active state in response to a connection of a pair of electrical contacts due to an expansion of the slit corresponding to the pill removed from the cavity of the pill package. The controller may be further configured to, for example, record the change in the state of the circuit as a removal event of a pill from the cavity of the pill package, where the change in the state of the circuit indicates a removal of a particular pill from a cavity of the pill dispensing device.

In some examples, the controller may be further configured to detect the change in the state of the circuit from a circuitry component of the lower portion of the pill dispensing device, the circuitry component configured to connect to each individual circuit. In examples, the circuitry may be connected to the controller via one or more contacts between the upper portion and the lower portion. The circuitry, for example, may be connected to the controller via a remote connection.

In some examples, the controller may be configured to report the record of pill removal to the remote monitoring service employing one or more of: a wired communication, a cellular wireless communication, an optical communication, a near field communication, a wireless local area network communication, and a wide area network communication. In further examples, the controller may be further configured to provide one or more of an audio and a visual alert to a user about the removal of the pill.

The present disclosure further describes an example method. The example method may manufacture a pill dispensing device to monitor pill removal. The example method may include, among other things, forming a rigid upper portion configured to accommodate insertion of a pill package and one of printing a circuit board on a composite sheet or embedding the circuit board into the composite sheet, where the circuit board may include a plurality of individual circuits. The example method may additionally include forming a plurality of slits in each individual circuit of the circuit board on the composite sheet and inserting the composite sheet including the printed circuit board between a top plate and a bottom plate, where each of the top plate and the bottom plate may include a plurality of openings corresponding to a location of the plurality of slits formed on the composite sheet. The example method may further include inserting the printed circuit board sandwiched between the top plate and the bottom plate within the upper portion and inserting the pill package between the upper portion and the composite sheet, such that each of a plurality of pill containing cavities in the pill package correspond to the plurality of slits formed in the composite sheet.

In examples, the method may additionally include integrating a pair of electrical contacts with each of the plurality of slits formed on the composite sheet, where the electrical contacts in each pair may be configured to be in contact with each other in a default active state prior to removal of a pill from a cavity of the pill package.

In further examples, the method may include forming one or more cutouts on one or both sides of each of the plurality of slits on the composite sheet and integrating a pair of electrical contacts with each of the one or more cutouts, where each pair of electrical contacts may be configured to be separated from each other in a default state prior to removal of a pill from a cavity of the pill package.

In some examples, the method may further include thermoforming a plurality of cavities in the upper portion, where each cavity corresponds to a location of each of the plurality of pill containing cavities of the pill package.

In further examples, the method may further include selecting a size of the each of the plurality of slits to ensure each slit opens when a pill may be removed from a cavity. The method may further include, for example, configuring the slit to separate in response removal of a pill from the cavity of the pill package. The method may additionally include after removal of the pill, configuring the slit to close after complete removal of the pill to return the individual circuit corresponding to the slit to a default state.

In some examples, the method may further include providing circuitry on the composite sheet, the circuitry configured to connect each of the individual circuits on the circuit board. The method may further include configuring the circuitry to detect a change in state of the circuit and to report the change in state of the circuit to a controller of the pill dispensing device.

In further examples, the method may further include configuring the controller to store each change in state of the circuit detected by the circuitry as a removal event. In examples, the method may further include configuring the controller to report a record of removal events to an external monitoring service and enabling the controller to communicate with the external monitoring service to report the record of removal events employing one or more of: a wired communication, a cellular wireless communication, an optical communication, a near field communication, a wireless local area network communication, and a wide area network communication.

In some examples, the method may further include printing the circuit board on the composite sheet employing one of a lithographic technique, a subtractive printing technique, a wet etching technique, an additive printing technique, a flexographic printing technique, a screen printing technique, an inkjet offset printing technique, and a liquid injection molding (LIM) technique.

There are various vehicles by which processes and/or systems and/or other technologies described herein may be effected (for example, hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility may be paramount, the implementer may opt for a mainly software implementation; or, yet again alternatively, the implementer may opt for some combination of hardware, software, and/or firmware.

The foregoing detailed description has set forth various examples of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, some aspects of the examples disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof, and that designing the circuitry and/or writing the code for the software and or firmware would be possible in light of this disclosure.

The present disclosure is not to be limited in terms of the particular examples described in this application, which are intended as illustrations of various aspects. Many modifications and variations can be made without departing from its spirit and scope Functionally equivalent methods and apparatuses within the scope of the disclosure, in addition to those enumerated herein, will be possible from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular examples only, and is not intended to be limiting.

In addition, the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

The terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims

What is claimed is:

1. A pill dispensing device to monitor pill removal, the pill dispensing device comprising:
    an upper portion including a plurality of cavities, the upper portion configured to accommodate insertion of a pill package;
    a lower portion formed from a locally or completely flexible or stretchable composite sheet, wherein the composite sheet includes a plurality of slits through the composite sheet, wherein each slit of the plurality of slits corresponds to a location of a respective one of the plurality of cavities of the upper portion, and wherein the lower portion further includes a top plate and a bottom plate, each of the top plate and the bottom plate including a plurality of openings corresponding to locations of the plurality of slits formed in the composite sheet; and
    a circuit board printed on or embedded into the composite sheet, wherein the circuit board includes one or more circuits to detect removal of pills through the plurality of slits in the composite sheet, wherein the one or more circuits each include a pair of electrical contacts having a first contact and a second contact at each of the plurality of slits, wherein the first contact is positioned at a first side of the slit and the second contact is positioned at an opposite side from the first side of the slit.

2. The pill dispensing device of claim 1, wherein the plurality of cavities of the upper portion correspond to a location of one or more pill containing cavities of the pill package and each of the one or more circuits corresponds to each of the plurality of slits in the composite sheet.

3. The pill dispensing device of claim 1, wherein at least a portion of the composite sheet includes a rigid structural element embedded into the composite sheet such that the composite sheet includes a rigid portion and a flexible portion.

4. The pill dispensing device of claim 1, wherein the first contact and the second contact of each of the pairs of electrical contacts are configured to be in contact with each other when the corresponding slit is closed to maintain a default active closed state for each individual circuit corresponding to the slit.

5. The pill dispensing device of claim 4, wherein the slit is configured to expand in response to removal of a pill from the pill package, causing the respective first contact and the respective second contact of each of the pairs of electrical contacts to separate and breaking an individual circuit corresponding to the slit when expanded and the separated respective first contact and respective second contact.

6. The pill dispensing device of claim 5, wherein the slit is configured to close following complete removal of the pill and to reconnect the pair of electrical contacts to restore the individual circuit corresponding to the slit to the default active closed state.

7. The pill dispensing device of claim 1, further comprising:
a pair of electrical contacts positioned on one or both sides of each of the plurality of slits, wherein each of the pair of electrical contacts are configured to be separated from each other when the slit is closed to maintain a default inactive state for each individual circuit corresponding to the slit and the pair of electrical contacts.

8. The pill dispensing device of claim 7, further comprising one or more cutouts on one or both sides of each of the plurality of slits, wherein each cutout houses the pair of electrical contacts in a default separated configuration when the slit is closed.

9. The pill dispensing device of claim 1, wherein the slit is configured to expand in response to removal of a pill from the pill package, causing the respective first contact and the respective second contact of the respective pair of electrical contacts within each cutout corresponding to the slit to contact each other and closing an individual circuit corresponding to the expanded slit and the respective first contact and the respective second contact.

10. A system to monitor pill removal from a pill dispensing device, the system comprising:
a pill dispensing device including:
an upper portion including a plurality of cavities, the upper portion configured to accommodate insertion of a pill package;
a lower portion formed from a locally or completely flexible or stretchable composite sheet, wherein the composite sheet includes a plurality of slits through the composite sheet, wherein each slit of the plurality of slits corresponds to a location of the plurality of cavities of the upper portion, wherein the lower portion is sandwiched between a top plate and a bottom plate, each of the top plate and the bottom plate including a plurality of openings corresponding to locations of the plurality of slits formed on the composite sheet; and
a circuit board printed on or embedded into the composite sheet, wherein the circuit board includes one or more circuits to detect removal of pills through the plurality of slits in the composite sheet, wherein the one or more circuits each include a pair of electrical contacts having a first contact and a second contact at each of the plurality of slits, wherein the first contact is positioned at a first side of the slit and the second contact is positioned at an opposite side from the first side of the slit;
a controller configured to detect a change in a state of the one or more circuits in response to removal of a pill from a cavity of the pill package through the slit in the lower portion; and
a remote monitoring service configured to store a record of the removal of the pill from the pill dispensing device.

11. The system of claim 10, wherein the controller is further configured to detect the change in the state of the circuit from a default active state to an inactive state in response to separation of a pair of electrical contacts due to an expansion of the slit corresponding to the pill removed from the cavity of the pill package.

12. The system of claim 10, wherein the controller is further configured to:
record a change in the state of the one or more circuits as a removal event of a pill from the cavity of the pill package, wherein the change in the state of the one or more circuits indicates a removal of a particular pill from a cavity of the pill dispensing device; and
detect the change in the state of the one or more circuits from a circuitry component of the lower portion of the pill dispensing device, the circuitry component configured to connect to each individual circuit of the one or more circuits.

13. The system of claim 12, wherein the circuitry is connected to the controller via one of: one or more contacts between the upper portion and the lower portion and a remote connection.

14. The system of claim 12, wherein the controller is configured to report the event to a remote monitoring service employing one or more of: a wired communication, a cellular wireless communication, an optical communication, a near field communication, a wireless local area network communication, and a wide area network communication.

15. A method to manufacture a pill dispensing device to monitor pill removal, the method comprising:
forming a rigid upper portion configured to accommodate insertion of a pill package;
one of printing a circuit board on a composite sheet or embedding the circuit board into the composite sheet, wherein the circuit board includes a plurality of individual circuits;
forming a plurality of slits in the composite sheet at each individual circuit of the circuit board, wherein each individual circuit includes a pair of electrical contacts having a first contact and second contact at each of the plurality of slits, wherein the first contact is positioned at a first side of the slit and the second contact is positioned at an opposite side from the first side of the slit;
inserting the composite sheet including the printed circuit board between a top plate and a bottom plate, wherein each of the top plate and the bottom plate includes a plurality of openings corresponding to a location of the plurality of slits formed in the composite sheet;
inserting the printed circuit board sandwiched between the top plate and the bottom plate within the upper portion; and
inserting the pill package between the upper portion and the composite sheet, such that each of a plurality of pill containing cavities in the pill package corresponds to the plurality of slits formed in the composite sheet.

16. The method according to claim 15, further comprising:
integrating a pair of electrical contacts with each of the plurality of slits formed on the composite sheet, wherein the electrical contacts in each pair are configured to be in contact with each other in a default active state prior to removal of a pill from a cavity of the pill package.

17. The method according to claim 15, further comprising:
forming one or more cutouts on one or both sides of each of the plurality of slits on the composite sheet; and
integrating the first contact and the second contact of each of the pairs of electrical contacts with each of the one or more cutouts, wherein each pair of electrical contacts are configured to be separated from each other in a default state prior to removal of a pill from a cavity of the pill package.

18. The method according to claim 15, further comprising:
thermoforming a plurality of cavities in the upper portion, wherein each cavity corresponds to a location of each of the plurality of pill containing cavities of the pill package;
selecting a size of the each of the plurality of slits to ensure each slit opens when a pill is removed from a cavity; and
configuring the slit to separate in response removal of a pill from the cavity of the pill package.

19. The method according to claim 18, further comprising:
configuring the slit to close after complete removal of the pill to return the individual circuit corresponding to the slit to a default state.

20. The method according to claim 15, further comprising:
one of printing or embedding the circuit board on the composite sheet employing one of a lithographic technique, a subtractive printing technique, a wet etching technique, an additive printing technique, a flexographic printing technique, a screen printing technique, an inkjet offset printing technique, and a liquid injection molding (LIM) technique.

* * * * *